United States Patent [19]

Van Assche et al.

[11] Patent Number: 5,981,852
[45] Date of Patent: *Nov. 9, 1999

[54] MODIFICATION OF SUCROSE PHOSPHATE SYNTHASE IN PLANTS

[75] Inventors: Charles Van Assche, Saint Cur sur Mer; Danielle Lando; Jean Michel Bruneau, both of Paris, all of France; Toni Alois Voelker, Davis, Calif.; Monica Gervais, Saint-Leu-La-Foret, France

[73] Assignee: Calgene LLC, Davis, Calif.

[ * ] Notice: This patent is subject to a terminal disclaimer.

[21] Appl. No.: 08/718,777

[22] Filed: Sep. 24, 1996

Related U.S. Application Data

[63] Continuation-in-part of application No. 08/175,471, Dec. 27, 1993, Pat. No. 5,665,892, which is a continuation of application No. 07/672,646, Mar. 18, 1991, abandoned.

[30] Foreign Application Priority Data

Jul. 20, 1990 [EP] European Pat. Off. ............... 90402084

[51] Int. Cl.$^6$ ................................ A01H 5/00; C12N 5/14; C12N 15/82
[52] U.S. Cl. ........................ 800/317.4; 435/419; 435/468; 800/284; 800/286; 800/287; 800/298; 800/317; 800/317.2
[58] Field of Search .................................. 536/23.2, 23.6, 536/24.1; 435/172.3, 320.1, 419, 325, 183, 468; 47/58; 800/205, DIG. 9, DIG. 42, DIG. 52, DIG. 56, 284, 286, 287, 298, 317, 317.2, 317.4

[56] References Cited

U.S. PATENT DOCUMENTS

| | | | |
|---|---|---|---|
| 5,536,653 | 7/1996 | Barry et al. | 435/172.3 |
| 5,665,892 | 9/1997 | Van Assche et al. | 800/205 |
| 5,750,869 | 5/1998 | Shewmaker et al. | 800/205 |

FOREIGN PATENT DOCUMENTS

| | | |
|---|---|---|
| 530978 | 10/1997 | European Pat. Off. . |
| 0 438 904 | 7/1991 | United Kingdom . |
| 0 530 978 | 3/1993 | United Kingdom . |
| WO 92/14831 | 9/1992 | WIPO . |
| WO 92/16631 | 10/1992 | WIPO . |
| WO 93/06711 | 4/1993 | WIPO . |
| WO 93/14212 | 7/1993 | WIPO . |
| WO 94/00563 | 1/1994 | WIPO . |
| WO 94/28146 | 12/1994 | WIPO . |

OTHER PUBLICATIONS

Micallef BJ, et al. "Altered photosynthesis, flowering, and fruiting in transgenic tomato plants that have an increased capacity for sucrose synthesis." Planta 196: 327–334, May 1995.
Koziel MG, et al. "Opitmizing expression of transgenes with an emphasis on post–transcriptional events." Plant Mol. Biol. 32: 393–405, 1996.
Stam M, et al. "The silience of genes in transgenic plants." Ann. Bot. 79: 3–12, 1997.
Smith CJS, et al. "Antisense RNA inhibition of polygalacturonase gene expression in transgenic tomatoes." Nature 334: 724–726, Aug. 25, 1988.
Worrell et al., *The Plant Cell* (1991) 3: 1121–1130.
Klann et al., *Plant Physiology* (1992) 99: 351–353.
Galtier et al., *Plant Physiology* (1993) 101:535–543.
Heineke et al., *Plant Physiology* (1992) 100: 301–308.
Lee et al., *Science* (1988) 239: 1288–1291.
Werr et al., *EMBO J.* (1985) 4: 1373–1380.
Preiss, *TIBS* (Jan., 1984) 24–27.
Micallef et al., *Planta* (1995) 196: 327–334.
Sonnewald et al., *Planta* (1993) 189: 174–181.
Klann et al., *Plant Physiology* (1993) 103: 863–870.
Kalt–Torres et al., *Physiol. Plantarum* (1987) 70: 653–658.
Kerr et al., *Planta* (1987) 170: 515–519.
Su et al., *Plant Physiol.* (1978) 61: 389–393.
Bruneau et al., *Plant Physiol.* (1991) 96: 473–478.

*Primary Examiner*—Lynette R. F. Smith
*Assistant Examiner*—Amy J. Nelson

[57] ABSTRACT

Sucrose phosphate synthase (SPS), a process for its preparation, its DNA, and utilization of DNA encoding SPS to modify the expression of SPS in the plant cells are provided. Methods and compositions for producing SPS protein and DNA encoding SPS from a number of sources are provided. Also provided are transgenes comprising DNA encoding SPS and methods for the production of transgenic plant cells and plants which have extra SPS activity, and thus an increased capacity to synthesize sucrose. Transgenic plant cells and plants with the additional SPS activity exhibit altered carbon partitioning, growth and development, and yield under a variety of conditions.

57 Claims, 24 Drawing Sheets

FIG.3

SPS 90 peptides

A8  ThrTrpIleLys

B4  TyrValValGluLeuAlaArg

B11 SerMetProProIleTrpAlaGluValMetArg

SPS 30 kd peptides

4K  LeuArgProAspGlnAspTyrLeuMetHisIleSerHisArg

12N TrpSerHisAspGlyAlaArg

```
EcoRI
GAATTCCGGC GTGGGCGCTG GGCTAGTGCT CCCGCAGCGA GCGATCTGAG AGAACGGTAG    60
         2
                                                   BamHI
AGTTCCGGCC GGGCGCGCGG GAGAGGAGGA GGGTCGGGCG GGGAGGATCC G ATG GCC    117
                                                     106  MET Ala
                        KpnI
GGG AAC GAG TGG ATC AAT GGG TAC CTG GAG GCG ATC CTC GAC AGC CAC    165
Gly Asn Glu Trp Ile Asn Gly Tyr Leu Glu Ala Ile Leu Asp Ser His
                              142

ACC TCG TCG CGG GGT GCC GGC GGC GGC GGC GGC GGG GAC CCC AGG        213
Thr Ser Ser Arg Gly Ala Gly Gly Gly Gly Gly Gly Asp Pro Arg

TCG CCG ACG AAG GCG GCG AGC CCC CGC GGC GCG CAC ATG AAC TTC AAC    261
Ser Pro Thr Lys Ala Ala Ser Pro Arg Gly Ala His Met Asn Phe Asn
                                                          SalI
CCC TCG CAC TAC TTC GTC GAG GAG GTG GTC AAG GGC GTC GAC GAG AGC    309
Pro Ser His Tyr Phe Val Glu Glu Val Val Lys Gly Val Asp Glu Ser
                                                   299
GAC CTC CAC CGG ACG TGG ATC AAG GTC GTC GCC ACC CGC AAC GCC CGC    357
Asp Leu His Arg Thr Trp Ile Lys Val Val Ala Thr Arg Asn Ala Arg
                            AB
```

FIG. 7B

```
                    XhoI
                     |
GAG CGC AGC ACC AGG CTC GAG AAC ATG TGC TGG CGG ATC TGG CAC CTC    405
Glu Arg Ser Thr Arg Leu Glu Asn Met Cys Trp Arg Ile Trp His Leu
                 374

GCG CGC AAG AAG CAG CTG GAG GGC ATC CAG AGA ATC TCG                453
Ala Arg Lys Lys Gln Leu Glu Gly Ile Gln Arg Ile Ser

GCA AGA AGG AAG GAA CAG GAG CAG GTG CGT GAG ACG GAG GAC            501
Ala Arg Arg Lys Glu Gln Glu Gln Val Arg Glu Thr Glu Asp

CTG GCC GAT CTG TCA GAA GGC AAG GGA AAG GGA GAC ATC GGC GAG        549
Leu Ala Asp Leu Ser Glu Gly Lys Gly Lys Gly Asp Ile Gly Glu

CTT GCG CCG GTT GAG ACC AAG AAG TTC CAG AGG AAC TTC TCT            597
Leu Ala Pro Val Glu Thr Lys Lys Phe Gln Arg Asn Phe Ser

HindIII
                                                |
GAC CTT ACC GTC TGG TCT GAC GAC AAT AAG GAG AAG CTT TAC ATT        645
Asp Leu Thr Val Trp Ser Asp Asp Asn Lys Glu Lys Leu Tyr Ile
                                                     635

GTG CTC ATC AGC GTG CAT GGT CTT GTT CGT GGA GAA AAC ATG GAA CTA    693
Val Leu Ile Ser Val His Gly Leu Val Arg Gly Glu Asn Met Glu Leu
```

FIG.7C

```
GGT CGT GAT TCT GAT ACA GGT GGC CAG GTG AAA TAT GTG GTC GAA CTT   741
Gly Arg Asp Ser Asp Thr Gly Gly Gln Val Lys Tyr Val Val Glu Leu
                                            ─────────────────
                                                   B4

GCA AGA GCG ATG TCA ATG ATG CCT GGA GTG TAC AGG GTG GAC CTC TTC   789
Ala Arg Ala Met Ser Met Met Pro Gly Val Tyr Arg Val Asp Leu Phe

ACT CGT CAA GTG TCA TCT CCT GAC GTG TAC GAC TGG AGC TAC GGT GAG CCA   837
Thr Arg Gln Val Ser Ser Pro Asp Val Tyr Asp Trp Ser Tyr Gly Glu Pro

ACC GAG ATG TTA TGC GCC GGT TCC AAT GAT GGA GAG GGG ATG GGT GAG   885
Thr Glu Met Leu Cys Ala Gly Ser Asn Asp Gly Glu Gly Met Gly Glu

AGT GGC GGA GCC TAC ATT GTG CGC ATA CCG TGT GGG CCG CGG GAT AAA   933
Ser Gly Gly Ala Tyr Ile Val Arg Ile Pro Cys Gly Pro Arg Asp Lys

TAC CTC AAG AAG GAA GCG TTG TGG CCT TAC CTC CAA GAG TTT GTC GAT   981
Tyr Leu Lys Lys Glu Ala Leu Trp Pro Tyr Leu Gln Glu Phe Val Asp

GGA GCC CTT GCG CAT ATC CTG AAC ATG TCC AAG GCT CTG GGA GAG CAG  1029
Gly Ala Leu Ala His Ile Leu Asn Met Ser Lys Ala Leu Gly Glu Gln

GTT GGA AAT GGG AGG CCA GTA CTG CCT TAC CTG ATA CAT GGG CAC TAT  1077
Val Gly Asn Gly Arg Pro Val Leu Pro Tyr Val Ile His Gly His Tyr

GCC GAT GCT GGA GAT GTT GCT CTC CTT TCT GGT GCG CTG AAT GTG  1125
Ala Asp Ala Gly Asp Val Ala Leu Leu Ser Gly Ala Leu Asn Val
```

FIG.7D

```
CCA ATG GTG CTC ACT GGC CAC TCA CTT GGG AGG AAC AAG CTG GAA CAA   1173
Pro Met Val Leu Thr Gly His Ser Leu Gly Arg Asn Lys Leu Glu Gln

CTG CTG AAG CAA GGG CGC ATG TCC AAG GAG GAG ATC GAT TCG ACA TAC   1221
Leu Leu Lys Gln Gly Arg Met Ser Lys Glu Glu Ile Asp Ser Thr Tyr

AAG ATC ATG AGG CGT ATC GAG GGT GAG GAG CTG GCC CTG GAT GCG TCA   1269
Lys Ile Met Arg Arg Ile Glu Gly Glu Glu Leu Ala Leu Asp Ala Ser

GAG CTT GTA ATC ACG AGC ACA AGG CAG GAG ATT GAT GAG CAG TGG GGA   1317
Glu Leu Val Ile Thr Ser Thr Arg Gln Glu Ile Asp Glu Gln Trp Gly
                             HindIII TTG TAC GAT GGA TTT GAT GTC AAG CTT GAG AAA GTG CTG AGG GCA CGG   1365
Leu Tyr Asp Gly Phe Asp Val Lys Leu Glu Lys Val Leu Arg Ala Arg
                                 1340
                                         NcoI
GCG AGG CGC GGG GTT AGC TGC CAT GGT CGT TAC ATG CCT AGG ATG GTG   1413
Ala Arg Arg Gly Val Ser Cys His Gly Arg Tyr Met Pro Arg Met Val
                                     1387

GTG ATT CCT CCG GGA ATG GAT TTC AGC AAT GTT GTA GTT CAT GAA GAC   1461
Val Ile Pro Pro Gly Met Asp Phe Ser Asn Val Val His Glu Asp
```

FIG.7E

```
ATT GAT GGG GAT GGT GAC GTC AAA GAT GAT ATC GTT GGT TTG GAG GGT    1509
Ile Asp Gly Asp Gly Asp Val Lys Asp Asp Ile Val Gly Leu Glu Gly

GCC TCA ATG CCC AAG TCA ATG CCC CCA ATT TGG GCC GAA GTG ATG CGG TTC    1557
Ala Ser Pro Lys Ser Met Pro Pro Ile Trp Ala Glu Val Met Arg Phe
                                    B11

CTG ACC AAC CCT CAC AAG CCG ATG ATC CTG GCG TTA TCA AGA CCA GAC    1605
Leu Thr Asn Pro His Lys Pro Met Ile Leu Ala Leu Ser Arg Pro Asp

CCG AAG AAG AAC ATC ACT ACC CTC GTC AAA GCC TTT GGA GAG TGT CGT    1653
Pro Lys Lys Asn Ile Thr Thr Leu Val Lys Ala Phe Gly Glu Cys Arg

CCA CTC AGG GAA CTT GCA AAC CTT ACT CTG ATC ATG GGT AAC AGA GAT    1701
Pro Leu Arg Glu Leu Ala Asn Leu Thr Leu Ile Met Gly Asn Arg Asp

GAC ATC GAC GAC ATG TCT GCT GGC AAT GCC AGT GTC CTC ACC ACA GTT    1749
Asp Ile Asp Asp Met Ser Ala Gly Asn Ala Ser Val Leu Thr Thr Val

CTG AAG CTG ATT GAC AAG TAT GAT CTG TAC GGA AGC GTG GCG TTC CCT    1797
Leu Lys Leu Ile Asp Lys Tyr Asp Leu Tyr Gly Ser Val Ala Phe Pro
                                              BglII
                                              1827

AAG CAT CAC AAT CAG GCT GAC GTC CCG GAG ATC TAT CGC CTC GCG GCC    1845
Lys His His Asn Gln Ala Asp Val Pro Glu Ile Tyr Arg Leu Ala Ala
```

FIG.7F

```
AAA ATG AAG GGC GTC TTC ATC AAC CCT GCT CTC GTT GAG CCG TTT GGT    1893
Lys Met Lys Gly Val Phe Ile Asn Pro Ala Leu Val Glu Pro Phe Gly

CTC ACC CTG ATC GAG GCT GCG GCA CAC GGA CTC CCG ATA GTC GCT ACC    1941
Leu Thr Leu Ile Glu Ala Ala Ala His Gly Leu Pro Ile Val Ala Thr
                              SalI
AAG AAT GGT GGT CCG GTC GAC ATT ACA AAT GCA TTA AAC AAC GGA CTG    1989
Lys Asn Gly Gly Pro Val Asp Ile Thr Asn Ala Leu Asn Asn Gly Leu
                        1958
                                                        HindIII
CTC GTT GAC CCA CAC GAC CAG AAC GCC ATC GCT GAT GCA CTG CTG AAG    2037
Leu Val Asp Pro His Asp Gln Asn Ala Ile Ala Asp Ala Leu Leu Lys
                                                            2036
CTT GTG GCA GAC AAG AAC CTG TGG CAG GAA TGC CGG AGA AAC GGG CTG    2085
Leu Val Ala Asp Lys Asn Leu Trp Gln Glu Cys Arg Arg Asn Gly Leu CGC AAC ATC CAC CTC TAC TCA TGG CCG GAG CAC TGC CGC ACT TAC CTC    2133
Arg Asn Ile His Leu Tyr Ser Trp Pro Glu His Cys Arg Thr Tyr Leu ACC AGG GTG GCC GGG TGC CGG TTA AGG AAC CCG AGG TGG CTG AAG GAC    2181
Thr Arg Val Ala Gly Cys Arg Leu Arg Asn Pro Arg Trp Leu Lys Asp
```

FIG.7G

```
                                                                              NcoI
ACA CCA GCA GAT GCC GGA GCC GAT GAG GAG TTC CTG GAG GAT TCC  2229
Thr Pro Ala Asp Ala Gly Ala Asp Glu Glu Phe Leu Glu Asp Ser
                                                              2229

ATG GAC GCT CAG GAC CTG TCA CTC CGT CTG TCC ATC GAC GGT GAG AAG  2277
Met Asp Ala Gln Asp Leu Ser Leu Arg Leu Ser Ile Asp Gly Glu Lys

AGC TCG CTG AAC ACT AAC GAT CCA CTG TGG TTC GAC CCC CAG GAT CAA  2325
Ser Ser Leu Asn Thr Asn Asp Pro Leu Trp Phe Asp Pro Gln Asp Gln

GTG CAG AAG ATC ATG AAC AAC ATC AAG CAG TCG GCG CTT CCT CCG  2373
Val Gln Lys Ile Met Asn Asn Ile Lys Gln Ser Ala Leu Pro Pro

TCC ATG TCC TCA GTC GCA GCC GAG ACA GGC AGC ACC ATG AAC AAA  2421
Ser Met Ser Ser Val Ala Ala Glu Thr Gly Ser Thr Met Asn Lys

TAC CCA CTC CTG CGC CGG CGC CGG CGC TTG GTC TTC ATA GCT GTG GAC  2469
Tyr Pro Leu Leu Arg Arg Arg Arg Arg Leu Val Phe Ile Ala Val Asp
                                                                        PstI
TGC TAC CAG GAC GAT GGC CGT GCT AGC AAG AAG ATG CTG CAG GTG ATC  2517
Cys Tyr Gln Asp Asp Gly Arg Ala Ser Lys Lys Met Leu Gln Val Ile
                                                                         2511
```

FIG. 7H

```
                                                                              BglII
                                                                              |
CAG GAA GTT TTC AGA GCA GTC CGA TCG GAC TCC CAG ATG TTC AAG ATC    2565
Gln Glu Val Phe Arg Ala Val Arg Ser Asp Ser Gln Met Phe Lys Ile
                                                                2562
          SalI
          |
TCA GGG TTC ACG CTG TCG ACT GCC ATG CCG TTG TCC GAG ACA CTC CAG    2613
Ser Gly Phe Thr Leu Ser Thr Ala Met Pro Leu Ser Glu Thr Leu Gln
                  2581
      PstI
      |
CTT CTG CAG CTC GGC AAG ATC CCA GCG ACC GAC TTC GAC GCC CTC ATC    2661
Leu Leu Gln Leu Gly Lys Ile Pro Ala Thr Asp Phe Asp Ala Leu Ile
                2622

TGT GGC AGC GGC AGC GAG GTG TAC TAT CCT GGC ACG GCG AAC TGC ATG    2709
Cys Gly Ser Gly Ser Glu Val Tyr Tyr Pro Gly Thr Ala Asn Cys Met

GAC GCT GAA GGA AAG CTG CGC CCA GAT CAG GAC TAT CTG ATG CAC ATC    2757
Asp Ala Glu Gly Lys Leu Arg Pro Asp Gln Asp Tyr Leu Met His Ile
                                                        ‾‾‾‾‾‾‾‾‾
                                                           4K
AGC CAC CGC TGG TCC CAT GAC GGC GCG AGG CAG ACC ATA GCG AAG CTC    2805
Ser His Arg Trp Ser His Asp Gly Ala Arg Gln Thr Ile Ala Lys Leu
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
         12M
```

FIG. 7I

```
ATG GGC GCT CAG GAC GGT TCA GGC GAC GCT GTC GAG CAG GAC GTG GCG   2853
Met Gly Ala Gln Asp Gly Ser Gly Asp Ala Val Glu Gln Asp Val Ala

TCC AGT AAT GCA CAC TGT GTC GCG TTC CTC ATC AAA GAC CCC CAA AAG   2901
Ser Ser Asn Ala His Cys Val Ala Phe Leu Ile Lys Asp Pro Gln Lys

GTG AAA ACG GTC GAT GAG ATG AGG GAG CGG CTG AGG CGT GGT CTC       2949
Val Lys Thr Val Asp Glu Met Arg Glu Arg Leu Arg Met Arg Gly Leu
                                    PstI
                                     |
CGC TGC CAC ATC ATG TAC TGC AGG AAC TCG ACA AGG CTT CAG GTT GTC   2997
Arg Cys His Ile Met Tyr Cys Arg Asn Ser Thr Arg Leu Gln Val Val
                                2972

CCT CTG CTA GCA TCA AGG TCA CAG GCA CTC AGG TAT CTT TCC GTG CGC   3045
Pro Leu Leu Ala Ser Arg Ser Gln Ala Leu Arg Tyr Leu Ser Val Arg

TGG GGC GTA TCT GTG GGG AAC ATG TAT CTG ATC ACC GGG GAA CAT GGC   3093
Trp Gly Val Ser Val Gly Asn Met Tyr Leu Ile Thr Gly Glu His Gly
         XbaI
          |
GAC ACC GAT CTA GAG GAG ATG CTA TCC GGG CTA CAC AAG ACC GTG ATC   3141
Asp Thr Asp Leu Glu Glu Met Leu Ser Gly Leu His Lys Thr Val Ile
             3103
```

FIG.7J

```
GTC CGT GGC GTC ACC GAG AAG GGT TCG GAA GCA CTG GTG AGG AGC CCA    3189
Val Arg Gly Val Thr Glu Lys Gly Ser Glu Ala Leu Val Arg Ser Pro

GGA AGC TAC AAG AGG GAC GAT GTC GTC CCG TCT GAG ACC CCC TTG GCT    3237
Gly Ser Tyr Lys Arg Asp Asp Val Val Pro Ser Glu Thr Pro Leu Ala

GCG TAC ACG ACT GGT GAG CTG AAG GCC GAC GAG ATC ATG CGG GCT CTG    3285
Ala Tyr Thr Thr Gly Glu Leu Lys Ala Asp Glu Ile Met Arg Ala Leu

AAG CAA GTC TCC AAG ACT TCC AGC GGC ATG TGAATTTGAT GCTTCTTTTA      3335
Lys Gln Val Ser Lys Thr Ser Ser Gly Met

CATTTTGTCCTTTTCTTCACTGCTATATAAAATAAGTTGTGAACAGTACCGGCGGGGTGTGT    3395

ATATATATATTGCAGTGACAAATAAAACAGGACACTGCTAACTATACTGGTGAATATACG      3455

EcoRI
                                                |
ACTGTCAAGATTGTATGCTAAGTACTCCATTTCTCAATGTATCAATCGGAATTC             3509
                                              3505
```

PCGN627 pCGN639 pCGN986

MODIFICATION OF SUCROSE PHOSPHATE SYNTHASE IN PLANTS

CROSS-REFERENCE TO RELATED APPLICATIONS

This application is a continuation-in-part of U.S. Ser. No. 08/175,471 filed Dec. 27, 1993, now U.S. Pat. No. 5,665,892, which is a continuation of U.S. Ser. No. 07/672,646 filed Mar. 18, 1991, now abandoned, which disclosures are hereby incorporated by reference.

INTRODUCTION

1. Technical Field

The present invention relates to the sucrose phosphate synthase (SPS) and DNA encoding SPS to modify the expression of SPS in the plant cells, plant parts and plants.

2. Background

Difficulties in the purification of sucrose phosphate synthase (SPS) from plants have interfered with efforts to characterize this enzyme. SPS catalyses the formation of sucrose phosphate, the sucrose precursor molecule, from fructose-6 phosphate and UDP-glucose in photosynthetically active plant cells. Sucrose phosphatase then acts on the sucrose phosphate moiety, in an irreversible reaction, to remove the phosphate and to release sucrose ready to translocate from the mature leaf (source) to any tissue requiring photoassimilate (sink), especially growing tissues including young leaves, seeds, and roots.

Because SPS is considered a rate limiting enzyme in the pathway providing sucrose to growing tissue, the study of SPS and its activity is of special interest. In a recent publication, Walker and Huber, *Plant Phys.* (1989) 89:518–524, the purification and preliminary characterization of spinach (*Spinachia oleracea*) SPS was reported. However, monoclonal antibodies specific to the spinach SPS were found to be non-reactive with all other plants tested, "closely related" and "relatively unrelated species", including corn (*Zea maize*), soybean (*Glycine max*), barley (*Hordeum vulgare*), and sugar beet (*Beta vulgaris*). Thus, additional purified sources of SPS enzyme are needed for effective characterization of this factor. Especially of interest is the characterization of the corn SPS because of its very high export rates, as compared for example, to SPS levels of activity as found in the leaves of soybean.

With the advent of biotechnology, the ability to modify various properties of plants, especially agronomically important crops, is of interest. In this regard, it would be useful to determine the coding sequence for an SPS gene to probe other crop sources, to use such coding sequences to prepare DNA expression constructs capable of directing the expression of the SPS gene in a plant cell and to express a DNA sequence encoding an SPS enzyme in a plant to measure the effects on crop yield due to the increased rate of sucrose translocation to growing tissues.

3. Relevant Literature

The following references are related to expression of SPS in transgenic plants: Sonnewald, et al. (1994) *Plant, Cell and Environment* 17:649–658; Worrell, et al. (1991) *The Plant Cell* 3:1121–1130; Micallef, et al. (1995) *Planta* 196:327–334; Foyer, et al. (1994) *Plant Physiol.*, 105(S), 23; Galtier et al. (1993) *Plant Physiol.* 101:535–543; and PCT Application No. WO 94/00563. The following references are related to isolation of DNA encoding SPS: Valdez-Alarcon et al., (1996) *Gene* 170(2):217–222; Sakamoto et al., (1995) *Plant Science* (Shannon) 112(2):207–217; Heese et al., (1995) *Mol. Gen. Genet.*, 247(4):515–520; Klein et al., (1993) *Planta* 190(4):498–510; Salvucci et al., (1993) *Plant Physiol.*, 102(2):529–536; Sonnewald et al., (1993) 189(2):174–181; and Herrera-Estrella et al., (1991) *J. Cell Biochem. Suppl.* 0 (15 Part A) 148.

SUMMARY OF THE INVENTION

Proteins having the sucrose phosphate synthase (SPS) activity, namely, a protein capable of catalyzing the formation of sucrose phosphate from fructose-6-phosphate and UDP-glucose substrates, substantially free of other proteins are provided. Among the preferred proteins of this invention are such proteins which are obtainable from corn or derived from the corn sucrose phosphate synthase. Also provided are nucleic acid constructs, vectors, plant cells, plant parts and plants containing at least one exogenously supplied copy of an SPS gene. The invention finds use in modifying carbohydrate partitioning in plant tissues and/or parts. Such modification can be used to alter plant growth, soluble solid content and/or sweetness, and/or to alter the sensitivity of plant growth to temperature and/or to levels of carbon dioxide and oxygen.

BRIEF DESCRIPTION OF THE FIGURES

In FIG. 2A, membrane is incubated in the presence of the SPB3-2-19 antibody; in FIG. 2B, membrane is incubated in the presence of an antibody not directed against SPS (negative control anti-neomycin monoclonal antibody); in FIG. 2C, membrane is incubated in the presence of the SPB13-2-2 antibody. The abbreviations used are as follows: M: standards of molecular weight radio-marked by $125_I$ (NEX-188 NEN) B-Galactosidase (116 kd), bovine albumin (68 kd), carbonic Anhydrase (29 kd), trypsic Inhibitor (20.1 kd), Alpha-Lactalbumin (14.4 kd), 150,000 cpm per lane; PA: proteins obtained after immunoaffinity chromatography (see below) with the SPB13-2-2 monoclonal antibody, about 40 micrograms of proteins per lane; H: Heparin fraction, about 40 micrograms of protein per lane.

FIG. 3 shows peptide sequences (SEQ ID NOS: 1–5) derived from SPS protein. All peptides are typed N->C terminal.

FIG. 4 shows oligonucleotides used for the PCR reactions CD3 (SEQ ID NOS: 10–11) and CD4 (SEQ ID NOS: 12–13) in relation to the peptides (antisense sequences are presented upside down). Arrows point to the direction the oligonucleotides will prime the polymerase.

FIG. 5A shows agarose gel electrophoresis of CD3 and CD4 PCR reactions. The sizes are given in kb. FIG. 5B shows autoradiograph of Southern blot of CD3 and CD4 PCF reactions probed with oligonucleotides 4k5 (SEQ ID NO: 14).

FIGS. 7A–7D shows the assembled SPS cDNA sequence (SEQ ID NO: 6). The sequences of clones SPS 90, SPS 61 and SPS 3 were fused at the points indicated in FIG. 6. The SPS reading frame is translated (SEQ ID NOS: 6–7). All SPS protein derived peptide sequences are indicated.

FIG. 9A shows a Comassie Blue-stained gel of total protein isolated from a 30 day old corn plant. M=size marker; R=roots; 1–8=leaf numbers counting from the bottom of the plant. Leaf 5 has been cut into 5 segments from the leaf tip (5a) to the end of the sheath (5c). PEP= phosphoenolpyruvate carboxylase. FIG. 9B shows the results of Western blot analysis using a mixture of antiSPS 30 and antiSPS 90 antisera against total plant protein isolated from a 30 day old corn plant. The signal corresponding to SPS appears at 120–140 kd.

FIG. 10A shows construction of pCGN627; FIG. 10B shows construction of pCGN639; and FIG. 10C shows construction of pCGN986.

DESCRIPTION OF THE SPECIFIC EMBODIMENTS

Figure 1:
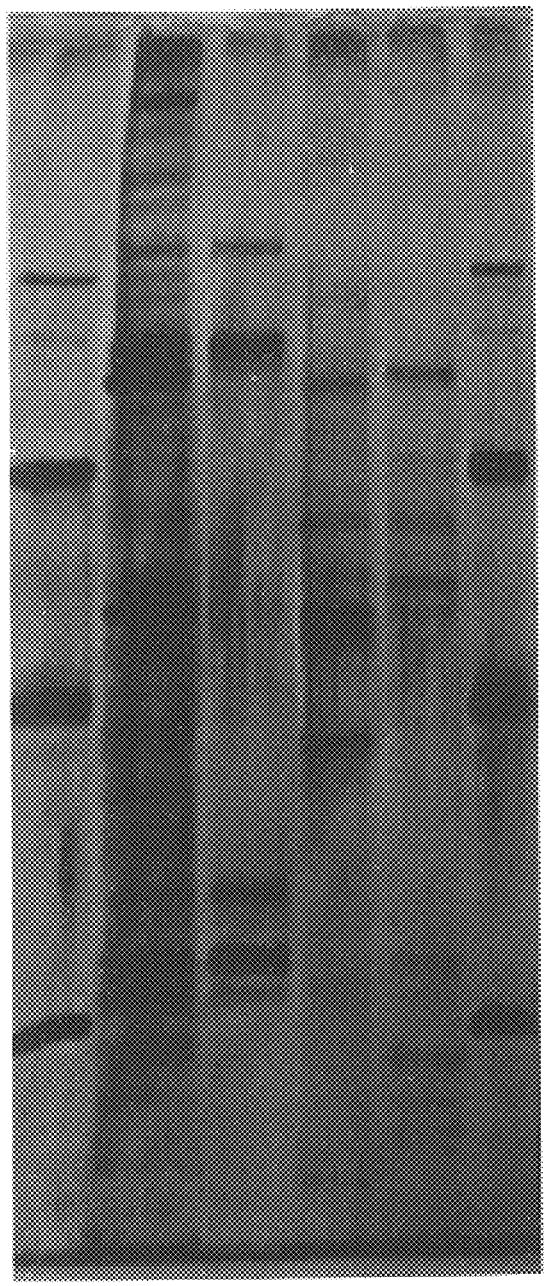
FIG. 1 shows an SDS-PAGE profile of corn SPS at various stages of SPS purification and the quality of the final preparation. Using an 8.5% acrylamide gel, reducing conditions and staining with silver nitrate. The abbreviations used are as follows: M: Standard of molecular weight B-Galactosidase (116 kd), bovine Albumin (68 kd), Egg Albumin (45 kd), carbonic Anhydrase (29 kd); H: Heparin fraction, 30 micrograms of proteins per well; FP: Final Preparation, 7.5 micrograms of proteins per well; FE: Final Extract, 7.5 micrograms of proteins per well; D: Fast-Flow DEAE fraction, 78.5 micrograms of proteins per well.

Transgenic plants and plant parts are provided which have altered carbon partitioning and end-product synthesis through expression of a transgene required for sucrose synthesis. Plants, plant parts, and plant cells transformed with one or more copies of a transgene comprising DNA encoding SPS and a transcriptional initiation region functional in plants are exemplified. The transgenic plants, cells and plant parts such as leaf, fruit and root are characterized by modified levels of SPS activity compared to controls. By "modified SPS activity" is intended an increase or decrease in sucrose synthesis. Modification of SPS activity according to the subject invention alters the carbon partitioning between source tissue and sink tissue through an increase or decrease in sucrose synthesis. Altered carbon partitioning is manifested by one or more changes in development, growth and yield through modification of end-product synthesis and conversion in general. The protein and DNA encoding SPS of the subject invention is obtainable from any number of sources which contain an endogenous SPS.

Among the preferred SPSs are those obtainable from corn or derived from corn SPS protein or nucleic acid using antibody and/or nucleic acid probes for SPS identification, amplification and isolation. The subject invention also provides a variety of SPS transgenes which have different promoter regions to regulate the transcription and level of SPS activity in plants or plant parts in a tissue-specific and growth-dependent manner. Among the preferred promoter regions are those which provide for leaf, fruit and/or root specific expression of SPS. Preferably, the DNA encoding a SPS of interest in operably linked in a sense or antisense orientation to a selected transcription initiation region to provide for a sufficient level of expression of SPS in the desired tissue or tissues.

An advantage of increasing or decreaseing SPS activity is the modification of sucrose synthesis, which is a key metabolic product that affects the interface between end-product synthesis and carbon partitioning for most plant systems. By "end-product" synthesis is intended the metabolic product interface between photosynthesis and plant growth and development. Information flow across the interface may occur by mass action or by signal transmission and transduction. Mass action effects occur when an increase in photosynthesis leads to faster growth resulting from an increase in the availability of photosynthate. Conversely, mass action feedback occurs when accumulation of end-products reduce the rates of photosynthetic reactions. Thus, an advantage of the subject invention is that modification of sucrose synthesis through SPS activity provides a central control point for modifying carbohydrate partitioning through end-product synthesis in a source tissue such as leaf and end-product conversion in a sink tissue such as growing leaf, fruit or root. For example, modulation of photosynthetic metabolism through expression of exogenous SPS is advantageously used to alter the synthesis of end-products such as starch, sucrose, glucose, fructose, sugar alcohols, and glycine and serine from photorespiratory metabolism. SPS preferably is used to modulate end product synthesis of non-phosphorylated products of metabolism. Another advantage is that SPS activity provides a means for altering plant growth and yield of specific plant cells, plant tissues, plant parts and plants. In addition, by modulating the ability of a plant to synthesize sucrose, the growth response of a plant under a variety of different environmental conditions can be affected including carbon dioxide utilization, oxygen sensitivity, temperature-dependent growth responsiveness and expression of endogenous genes responsive to sugar content in general. Manipulation of growth conditions also permits the modulation of metabolism and the activity of the SPS transgene, for example, through light-mediated activation or deactivation of the SPS transgene and its product. Another advantage is the modification of overall soluble solids such as starch, sucrose, glucose and fructose in sink tissue such as fruit or root. SPS activity and sugar content also permit manipulation of endogenous gene expression and/or enzyme activity in the plant, such as the endogenous acid invertase found in ripening fruit to increase glucose and fructose levels as well as acid content. An additional advantage is that the onset of flowering, fruit number, mass, dimensions, and overall morphology can be modified by altering carbon partitioning. Thus, the subject invention permits the obtention of any transgenic plant or plant part which have any one of several readily selectable phenotypes related to SPS transgene expression and SPS protein activity.

By "protein" is intended any amino acid sequence, including a protein, polypeptide, or peptide fragment, whether obtained from plant or synthetic sources, which demonstrates the ability to catalyze the formation of sucrose phosphate. An SPS of this invention includes sequences which are modified, such as sequences which have been mutated, truncated, increased in size, contain codon substitutions as a result of the degeneracy of the DNA code, and the like as well as sequences which are partially or wholly artificially synthesized, so long as the synthetic sequences retain the characteristic SPS activity.

By "substantially free from other proteins" is meant that the protein has been partially purified away from proteins found in the plant cell. Such a protein of this invention will demonstrate a specific enzymatic activity of at least greater than 0.05, more preferably at least greater than 0.30, wherein specific enzymatic activity (sA) is measured in units which correspond to 1 μm (micromole) of sucrose formed per minute per mg of protein at 37° C. In a more preferred embodiment, the protein will demonstrate even more improved sA and increased purification factors (see, Table 5).

In the subject invention, purification of corn SPS protein is exemplified. SPS from sources in addition to corn are obtainable by a variety of standard protocols employing protein properties, amino acid and nucleic acid information derived from corn SPS. For example, antibody or nucleic acid probes derived from sequencing information permit isolation of a gene or parts of the gene including genomic DNA and cDNA encoding the target SPS of interest. For this purpose, degenerate and non-degenerate probes from hybridization studies with parts or all of the corn SPS sequence can be used for identification, isolation and amplification of a gene or fragments encoding the SPS of interest. The SPS gene or fragments are assembled and evaluated by conventional recombinant DNA and biochemical techniques, and through nucleic acid and amino acid sequence database comparisons. As an example, SPSs derivable from corn SPS sequences in this manner include potato, spinach, rice and sugar beet. In vitro and in vivo expression systems can be used to produce and test the SPS. The SPS activity can be evaluated by measuring formation of sucrose phosphate from fructose-6-phosphate and UDP-glucose substrates.

The exemplified invention relates to the enzyme comprising a corn SPS having a molecular weight from about 110 to 130 kilodalton (kd) and a specific activity of greater than 0.05 U. The invention relates more particularly to the enzyme comprising a corn SPS having a specific activity of about 25 U.

In order to obtain the nucleic acid sequences encoding the SPS, especially corn SPS, substantially purified SPS was required. As demonstrated more fully in the examples, corn SPS purified 500-fold was obtained in small quantities which were then ultimately used to obtain the peptide sequence which in turn led to the determination of the cDNA sequence.

Among the preferred proteins of the invention are the proteins having the above definition with a molecular weight from about 110 to about 130 kd, having the form of a monomer, a dimer or a tetramer and their derivatives, comprising at least one peptide having the following amino acid sequence:
Thr-Trp-Ile-Lys (SEQ ID NO: 1)
Tyr-Val-Val-Glu-Leu-Ala-Arg (SEQ ID NO: 2)
Ser-Met-Pro-Pro-Ile-Trp-Ala-Glu-Val-Met-Arg (SEQ ID NO: 3)
Leu-Arg-Pro-Asp-Gln-Asp-Tyr-Leu-Met-His-Ile-Ser-His-Arg (SEQ ID NO: 4)
Trp-Ser-His-Asp-Gly-Ala-Arg (SEQ ID NO: 5)

The invention also relates to a process to prepare proteins as above defined, having the following steps: (a) extracting SPS from parts containing SPS, which are preserved at low temperature, by grinding, centrifugation and filtration; (b) increasing the rate of SPS extraction from the extract so obtained by precipitation in an appropriate solvent, centrifugation and solubilization of the precipitate in a buffer solution; (c) purifying the protein so obtained by chromatography and, if desired, (d) preparing hybridomas, and monoclonal antibodies from an antigenic solution obtained at step (a), (b), or (c) above; (e) screening the hybridomas and raising monoclonal antibodies specifically directed against SPS; and (f) further purifying the SPS obtained at step (a), (b), or (c) with the monoclonal antibodies prepared.

The invention more precisely relates to a process of preparation of corn SPS having the following steps: (a) extracting SPS from parts of corn plants by grinding, centrifugation, and filtration; (b) increasing the rate of SPS extraction from the extract so obtained by precipitation in polyethyleneglycol (PEG), centrifugation and solubilization of the precipitate obtained in a buffer solution; (c) purifying the protein so obtained by low pressure anion exchange chromatography and by chromatography on heparin sepharose, then by anion exchange high performance chromatography; (d) purifying the active pools by passage on two high performance chromatography columns, and if desired; (e) preparing hybridomas and monoclonal antibodies from an antigenic solution prepared from steps (a), (b), or (c); (f) screening the hybridomas and raising the monoclonal antibodies specifically directed against SPS; and (g) purifying the SPS preparation with the monoclonal antibodies so obtained.

Preferably the corn is a corn Pioneer corn hybrid strain 3184, the parts of plants are leaves which are kept at low temperature, for example between −50° C. and −90° C., and purification in the polyethyleneglycol is realized first by precipitating at a final concentration in PEG about 6%, and then by precipitating at a final concentration of about 12%. The various chromatographies are performed in the following way: 1st chromatography, DEAE sepharose; 2nd chromatography, heparin sepharose (at this stage, the preparation obtained may be kept several days without loss of activity); 3rd chromatography, Mono Q chromatography; 4th chromatography, HPLC hydroxyapatite; and 5th chromatography, HPLC hydroxyapatite.

A variety of additional protein fractionation methods can be combined to generate a suitable purification scheme for SPS proteins and peptides from corn and those in addition to corn. If only very small amounts of denatured protein are needed, a high resolution technique may be used such as two-dimensional gel electrophoresis to obtain the protein in one step. When retention of activity is desired, a series of purification steps are designed to take advantage of different properties of the the SPS of interest such as precipitation properties, charge, size, adsorptive properties and affinity properties as demonstrated for corn SPS. In general, purification follows the initial extraction and preparation of total protein, bulk precipitation followed by chromatographic procedures such as ion exchange, adsorption, gel filtration, affinity resins and non-denaturing electrophoresis methods. The proteins can be further purified if desired, when retention of activity is less important, by electrophoretic procedures including native or denaturing polyacrylamide gel electrophoresis, isoelectric focusing and two dimensional gel electrophoresis.

During the different steps of purification and thereafter, the SPS activity can be measured by two methods: (a) a method based on a calorimetric test or resorcinol test; and (b) a method based on the amount of one of the products formed during the transformation reactions where SPS is involved. Both methods are detailed in the experimental part detailed hereunder. Antibodies to SPS are prepared as follows, or by other methods known to those skilled in the art.

Mice are immunized with several injections of enzymatic preparations. Different kinds of mice may be used, for example BALB/c. The antigen can be provided in complete Freunds adjuvant then in incomplete Freunds adjuvant. Several injections in mice are realized: good results have been obtained with three injections of Mono Q, pools, (see above purification scheme) followed by three injections of final pools (days 0, 14, 27, 60, 90 and 105 for example). The first injections are administered sub-cutaneously, for example in the cushions, and the feet, the last injection is administered intravenously, in the tail for example.

The preparation of spleen cellular suspensions from animals immunized as described above is made in a conventional way. The steps of fusion with myeloma cells, of conservation of the hybridoma, of cloning, of antibodies production are made by conventional ways. To detect the hybridoma secreting the monoclonal antibodies raised against the antigen, two methods are used to select antibodies: a method of detection of antibodies as inhibitor of SPS activity; and a method of detection of antibodies precipitating SPS activities. In a preferred embodiment, these methods are the methods described in the experimental section detailed hereunder.

Among the objects of the invention, are also provided lines of hybridoma cells, and in particular hybridoma cells described as:

SPA 2-2-3:I-971
SPA 2-2-22:I-970
SPA 2-2-25:I-972
SPB 3-2-19:I-973
SPB 5-2-10:I-974
SPB 5-4-2:I-975
SPB 13-1-7:I-976
SPB 13-2-2:I-977.

Deposits of these hybridoma cells were made at the C.N.C.M. (Institut Pasteur Paris) on Jun. 11, 1990. The invention relates also to monoclonal antibodies specifically directed against SPS.

The invention relates also to a process of preparation of proteins as defined above characterized in that a preparation containing the so-called proteins is purified on a chromatography column having monoclonal antibodies as defined above specifically raised against the proteins.

The invention relates also to cDNA coding for proteins as defined above, specially cDNA coding for corn SPS. Among the preferred cDNA preferred is the cDNA with the nucleotide sequence represented in FIG. 7 (SEQ ID NO: 6). Thus, this invention relates to an extrachromosomal DNA sequence encoding a SPS as defined above. Any DNA sequence which is not incorporated into the genome of a plant is considered extrachromosomal, i.e., outside of the chromosome, for purposes of this invention. This includes, but is not limited to cDNA, genomic DNA, truncated sequences, single stranded and double stranded DNA. In a preferred embodiment, the DNA sequence is cDNA. In a different preferred embodiment, the DNA sequence is obtainable from corn or is derived from the corn DNA sequence.

Among the preferred proteins and nucleic acid sequences of the invention is corn SPS. The corn SPS is represented in FIG. 1, which shows the presence of proteins at about 120, 95 and 30 kd. The proteins shown at 95 and 30 kd are considered to be breakdown products of the protein shown at 120 kd. The complete protein is believed to be a di- or tetrameric protein having as the basic sub-unit from about a 110 to about a 130 kd protein. The complete cDNA sequence of the corn SPS is shown in FIG. 7 (SEQ ID NO: 6).

The cDNA coding for sucrose phosphate synthase has been prepared in the following way: (1) sequencing of peptide fragments from purified SPS. With the purified preparations of SPS previously obtained, following separation on an acrylamide gel, a 120 kd minor band (corresponding to the total protein sequence) and two 90 kd and 30 kd major bands are obtained. Both major polypeptides are separated by electrophoresis and electroeluted. By trypsin digestion and sequencing of the fragments so obtained, the sequence of 5 peptides has been determined. This amino acid sequence makes it possible to determine the corresponding degenerate nucleotide sequence.

(2) Corn leaf isolation. Total RNA is isolated according to Turpen and Griffith (1986, *Biotechniques* 4:11–15) for poly (A) RNA preparation, the standard oligo dT cellulose column is used.

(3) cDNA library construction. cDNA is synthesized using the protocol of a kit supplied by Promega except that M-MLV reverse transcriptase is used instead of AMV reverse transcriptase. The length of cDNA obtained is from 500 to several thousand base pairs. EcoRI linkers are added to the blunt ended cDNA and this material is cloned into a second generation lambda GT11 expression vector. Total library size is about $1.5 \times 10^6$ plaques.

(4) Utilization of PCR to synthesizing a nucleotide sequence specific for SPS. The oligonucleotides derived from peptides B11 (SPS 30 kd) (SEQ ID NO: 3) and 4K (90 kd) (SEQ ID NO: 4) described in FIG. 3 are used as primers in a PCR reaction. It has been assumed that peptides derived from SPS 30 and SPS 90 are degradation products of protein SPS 120 kd, and that the peptides derived from SPS and SPS 90 are encoded by the same RNA.

Figure 4:
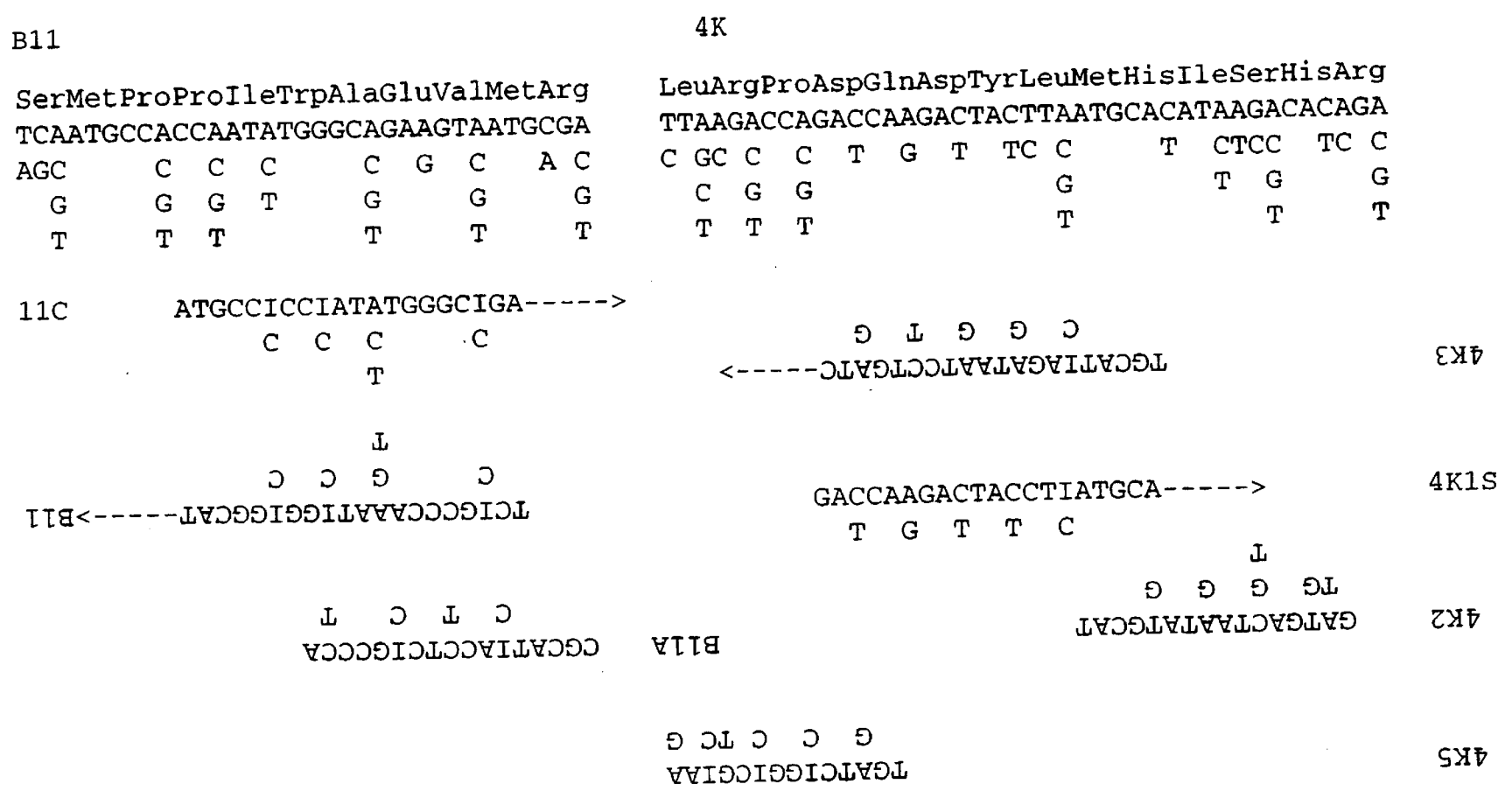
Figure 5A:
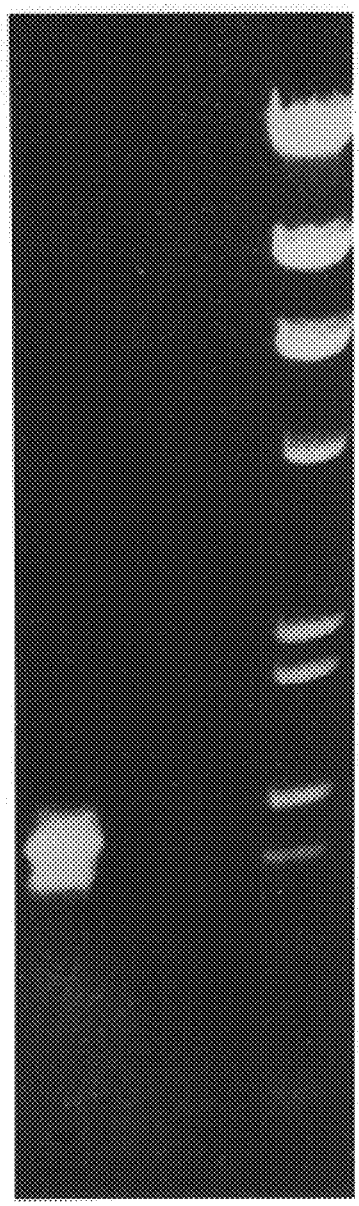
FIGS. 5A–5B shows the characterization of CD3 and CD4 PCR reactions.
Figure 5B:
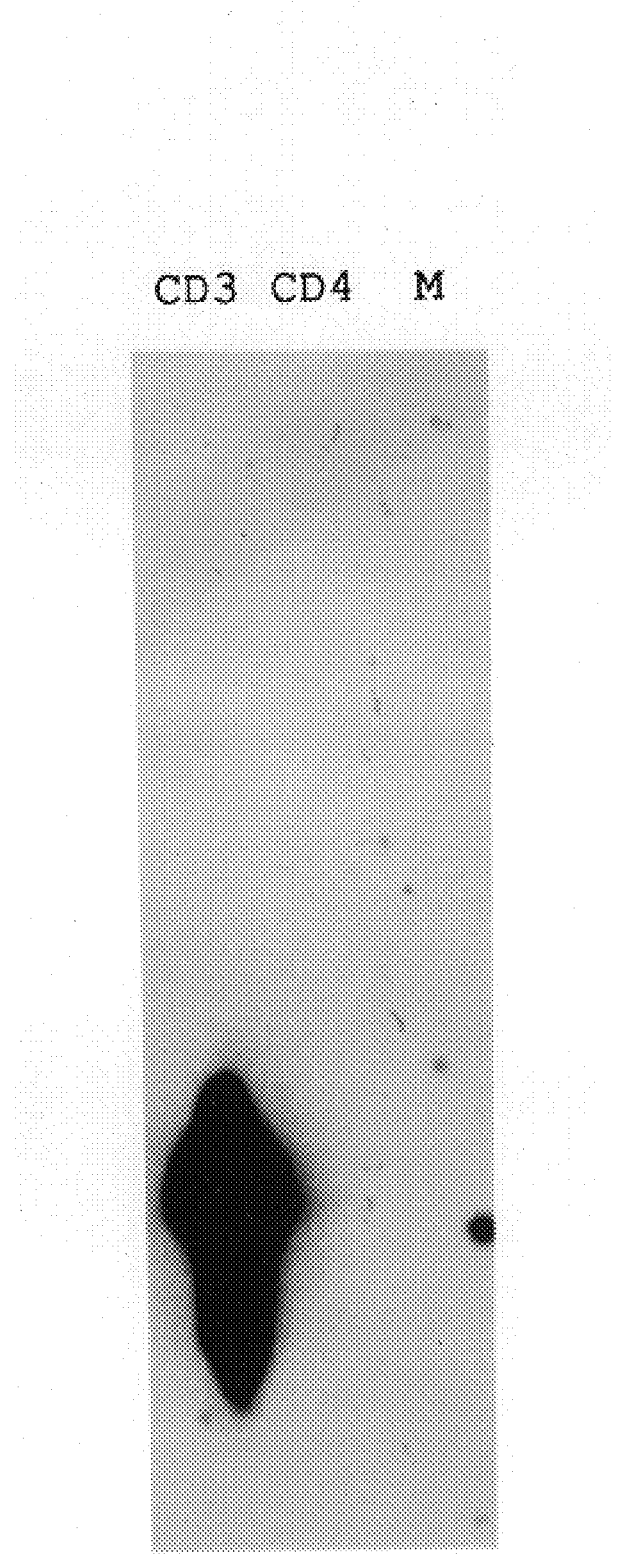

With this hypothesis, by using in proper polarity pairs of oligonucleotides corresponding to the peptidic sequences in a PCR reaction, one may obtain the synthesis of the DNA, connecting the two location. Since it is a priori not know in which order the peptides are located relative to each other, one has to do the two different possibilities (FIG. 4). Only the oligonucleotide couple CD3 synthesizes a cDNA of defined length (1200 bp) (FIG. 5).

Figure 6:
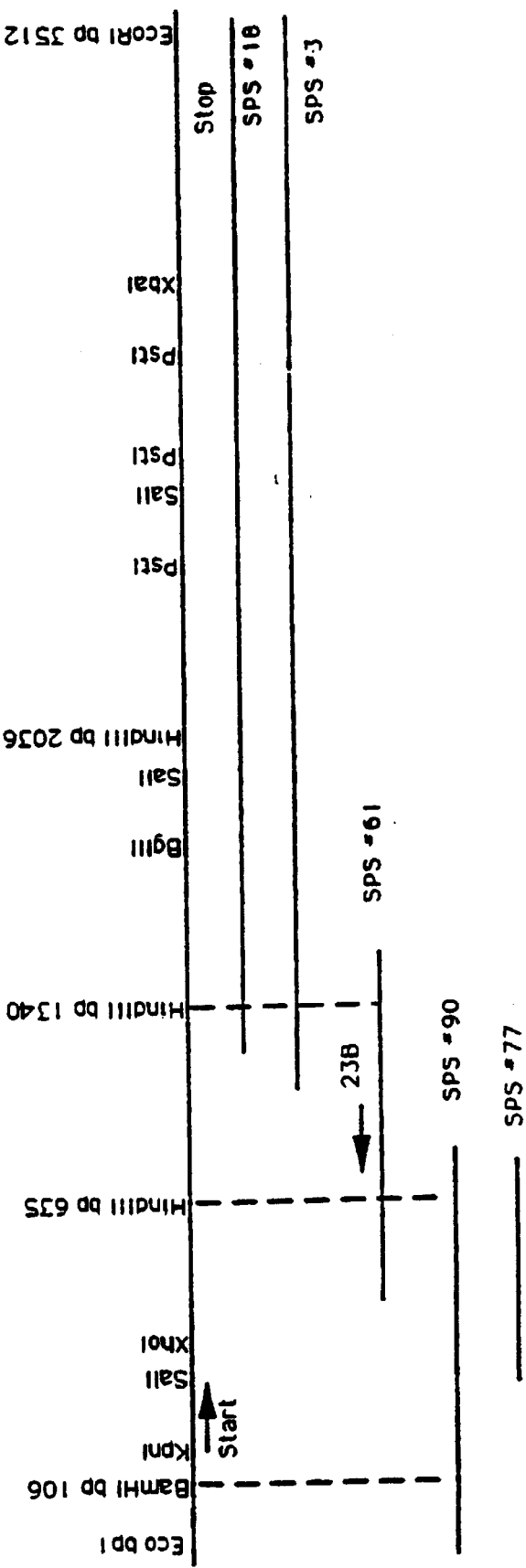
FIG. 6 shows schematic diagrams representing SPS cDNA and selected clones. The upper bar represents the entire 3509 bp combined map. Translation stop and start points are indicated.

(5) cDNA library screening. When 250,000 lambda clones GT11 are screened using the 1200 bp long PCR cDNA, 16 positives are obtained. Sizes of the inserts ranged from 0.3 kb to 2.8 kb (see FIG. 6 for the two longest clones). The sequence is not complete in 5'. In a second round of library screening with a 400 bp DNA fragment corresponding to the most 5' fragment of the clone SPS 3, a SPS 61 clone extending further 5' without having the 5' end of the reading frame is obtained (FIG. 6).

(6) Creation and screening of a second cDNA libray in order to clone the 5' sequence of cDNA coding for SPS. An oligonucleotide complementary to the 5' sequence of clone SPS 61 is used as a primer for cDNA synthesis. After second strand reaction is completed, the cDNA is cloned into bacteriophage lambda GT11. The library includes about one million clones. The SPS 90 and SP 77 were obtained by screening this library with SPS 61 (FIG. 6).

(7) The assembled SPS reading frame. DNA sequences which encode the SPS may be employed as a gene of interest in a DNA construct or as probes in accordance with this invention. When provided in a host cell, the sequence can be expressed as a source of SPS. More preferred is the SPS sequence in a vegetal cell under the regulatory control of a transcriptional and translational initiation region functional in plants. Vegetal cell means any plant cell being able to form undifferentiated tissues as callus or differentiated tissues as embryos, parts of plants, whole plants or seeds. Plants means for example plants producing grain seeds such as cereals, and includes wheat, barley, corn, and oat; leguminous plants such as soybean; oleaginous plants such as turnesol; tuberous plants such as potato; plants with roots such as beet; and fruit such as tomato. The sucrose phosphate synthase is a key enzyme, in sucrose regulation mechanisms, but also in carbon partitioning regulation between starch and sucrose during photosynthesis (see J. Preiss, Tibs January 1984, page 24, or Stitt and Coll, (1987) *Biochemistry of Plants,* 10:3–27). Of particular interest are plants of the nightshade family Solanaceae, including the genetically similar but physiologically disparate plants potato (*Solanium tuberosum*) and tomato (*Hycopersicon esculentum*).

When provided in a DNA construct for integration into a plant genome, the sequence can be in a sense orientation or anti-sense orientation. By increasing the amount of SPS available to the photosynthetically active plant cell by the expression of additional SPS, an increased flow of sucrose can be provided to growing tissues resulting, for example, in increased plant yields; by decreasing the amount of SPS available to the photosynthetically active plant cell, the rate of sucrose release from the plant cell may be hindered, resulting in less new plant growth. Controlling the rate of transport and the amount of sucrose available to growing tissues can be used to increase or decrease the total solids in a plant sink tissue from a given ratio of total solids per unit weight sink tissue. Total solids include soluble solids and insoluble solids such as sugars, starches and cellulose. Of particular interest are the soluble solids, which include the sugars sucrose, fructose, and glucose, soluble organics, polymers and other soluble components of cells. Increased total solids in a plant sink tissue may be in the form of an increase in glucose and/or fructose levels. Where the increase comprises fructose, for example, the resulting phenotype is increased sweetness. Where fructose levels are lowered a reduced sweetness phenotype is produced. Of particular interest is fruit having a modified sweetness phenotype. Increasing or decreasing the flow and/or amount of sucrose available to fruit tissue increases or decreases the conversion of sucrose to glucose and fructose by acid invertase, and thus the sweetness of fruit. In tomato fruit, for example, glucose and fructose are produced from sucrose by a vacuolar acid invertase that is active during fruit ripening. As fructose is twice as sweet on a molar basis as glucose, an increase in fructose levels or a fructose to glucose ratio can result in an increased sweetness of the fruit. Of particular interest is fruit of the plant family Solanaceae. Sink tissue solids can be modified with SPS levels and/or activity in conjunction with endogenous sucrose and starch metabolizing enzymes, such as acid invertase for sucrose and glycogen synthase for starch. Modification can be used to enhance or inhibit enzymatic activity, for example through sense or antisense expression. By increasing or decreasing SPS activity in plants, the interaction between photosynthesis and the synthesis of end products, such as sucrose and starch, can be modified. Of particular interest is the modification of the starch to sucrose ratio in a vegetal cell through the expression of a transgene encoding SPS. Modifying the starch to sucrose ratio in vegetal cell may transduce the affect through end-product synthesis, signal transduction and/or translocation to other vegetal cells, particularly the vegetal cells of leaf, fruit and root. In some plants, the change in carbohydrate partitioning can also affect the sensitivity of the altered plant to carbon dioxide and oxygen. Increasing sucrose synthesis can result in greater capacity for photosynthesis at elevated carbon dioxide, particularly in the potato. Conversely, decreasing sucrose synthesis (increasing starch synthesis) induces oxygen insensitivity. Such an effect can be obtained by expressing antisense SPS.

By "obtainable from corn" is meant that the sequence, whether an amino acid sequence or nucleic acid-sequence, is related to a corn SPS, including a SPS recovered through use of nucleic acid probes, antibody preparations, sequence comparisons or derivatives obtained through protein modeling or mutagenesis for example. Thus, one skilled in the art will readily recognize that antibodies, nucleic acid probes (DNA and RNA) and the like can be prepared and used to screen other plant sources for SPS and recover it. Typically, a homologously related nucleic acid sequence will show at least about 60% homology, and more preferably at least about 70% homology between the corn SPS and the given plant SPS of interest, excluding any deletions which may be present. Homology is found when there is an identity of base pairs and can be determined upon comparison of sequence information, nucleic acid or amino acid, or through hybridization reactions conducted under relatively stringent conditions, e.g., under conditions where there is a fairly low percentage of non-specific binding with corn SPS probes.

Probes can be considerably shorter than the entire sequence, but should be at least about 10, preferably at least about 15, more preferably at least 20 nucleotides in length. Longer oligonucleotides are also useful, up to full length of the gene encoding the polypeptide of interest. Both DNA and RNA probes can be used. A genomic library prepared from the plant source of interest can be probed with conserved sequences from corn SPS to identify homologously related sequences. Use of the entire corn SPS cDNA may be employed if shorter probe sequences are not identified. Positive clones are then analyzed by restriction enzyme digestion and/or sequencing. In this general manner, one or more sequences can be identified providing both the coding region, and the transcriptional regulatory elements of the SPS gene from such plant source. As an example, probes derived from corn SPS are used for isolating SPS from corn and sources in addition to corn. A probe or a battery of probes representing all or segments of the SPS coding region of corn SPS are preferably used. The corn SPS sequences can be compared by conventional gene bank searches and the conserved and nonconserved regions used in the design of additional probes if needed. In addition, the conserved and nonconserved regions for probe design are identifiable through standard hybridization techniques or, for example, by comparing amino acid and/or nucleic acid sequences of corn SPS to SPS sequences from diverse sources including rice, potato, sugar beet, spinach ,or *Arabidopsis thaliana*, which is a flowering plant member of the mustard family Brasicaceae.

In use, probes are typically labeled in a detectable manner (for example with $^{32}$P-labelled or biotinylated nucleotides) and are incubated with single-stranded DNA or RNA from the plant source in which the gene is sought, although unlabeled oligonucleotides are also useful. Hybridization is detected by means of the label after single-stranded and double-stranded (hybridized) DNA or DNA/RNA have been separated, typically using nitrocellulose paper or nylon membranes. Hybridization techniques suitable for use with oligonucleotides are well known to those skilled in the art.

From the cDNA sequences, one skilled in the art can obtain the corresponding genomic DNA sequences related thereto to obtain the coding region of the SPS, including intron sequences, transcription, translation initiation regions and/or transcript termination regions of the respective SPS gene. The regulatory regions can be used with or without the SPS gene in various probes and/or constructs. The complete SPS reading frame can be assembled using restriction enzyme fragments of SPS 90, SPS 61 and SPS 3, see FIG. 6.

When expressed in *E. coli*, the SPS cDNA produces a protein which is recognized by anti-SPS antisera and has the same electrophoretic mobility as SPS extracted from corn leaves. We show that this *E. coli* SPS is as active as plant SPS, i.e. for complete enzymatic activity in *E. coli* no other plant factor is needed but the SPS cDNA.

Plants obtained by the method of transformation and containing fusions of SPS cDNA to tissue specific promoters in order to modify or alter the composition of certain plant organs are also included.

A DNA construct of this invention can include transcriptional and translational initiation regulatory regions homologous or heterologous to the plant host. Of particular interest are transcriptional initiation regions from genes which are present in the plant host species, for example, the tobacco ribulose biphosphate carboxylase small subunit (SSU) transcriptional initiation region; the cauliflower mosaic virus (CaMV) 35S transcriptional initiation region, including a "double" 35S CaMV promoter, the tomato fruit-specific E8 (E8) transcriptional initiation region, and those associated with T-DNA, such as the opine synthase transcriptional initiation region, e.g., octopine, mannopine, agropine, and the like.

Any one of number of regulatory sequences may be preferred in a particular situation, depending upon whether constitutive or tissue and/or timing induced transcription is desired, the efficiency of a particular promoter in conjunction with the heterologous SPS, the ability to join a strong promoter with a control region from a different promoter to provide for inducible transcription, ease of construction and the like. For example, tissue specific promoters can be employed to selectively modify or alter the composition of certain plant organs. Promoters which function in, or are specific by fruit, root and/or leaf are examples. These regulatory regions find ample precedence in the literature.

The termination region may be derived from the 3'-region of the gene from which the initiation region was obtained, from the SPS gene, or from a different gene. Preferably the termination region will be derived from a plant gene, particularly, the tobacco ribulose biphosphate carboxylase small subunit termination region; a gene associated with the Ti-plasmid such as the octopine synthase termination region or the tml termination region.

In developing the expression cassette, the various fragments comprising the regulatory regions and open reading frame may be subjected to different processing conditions, such a ligation, restriction, resection, in vitro mutagenesis, primer repair, use of linkers and adapters, and the like. Thus, nucleotide transitions, transversions, insertions, deletions, or the like, may be performed on the DNA which is employed in the regulatory regions and/or open reading frame.

During the construction of the expression cassette, the various fragments of the DNA will usually be cloned in an appropriate cloning vector, which allows for amplification of the DNA, modification of the DNA or manipulation by joining or removing of the sequences, linkers, or the like. Normally, the vectors will be capable of replication in at least a relatively high copy number in E. coli. A number of vectors are readily available for cloning, including such vectors as pBR322, pUC series, M13 series, etc. The cloning vector will have one or more markers which provide for selection or transformants. The markers will normally provide for resistance to cytotoxic agents such as antibiotics, heavy metals, toxins, or the like. By appropriate restriction of the vector and cassette, and as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

The manner of transformation of *E. coli* with the various DNA constructs (plasmids and viruses) for cloning is not critical to this invention. Conjugation, transduction, transfection or transformation, for example, calcium phosphate mediated transformation, may be employed.

In addition to the expression cassette, depending upon the manner of introduction of the expression cassette into the plant cell, other DNA sequences may be required. For example when using the Ti- or Ri-plasmid for transformation of plant cells, as described below, at least the right border and frequently both the right and left borders of the T-DNA of the Ti- or Ri-plasmids will be joined as flanking regions to the expression cassette. The use of T-DNA for transformation of plant cells has received extensive study and is amply described in *Genetic Engineering, Principles and Methods* (1984) Vol 6 (Eds. Setlow and Hollaender) pp. 253–278 (Plenum, N.Y.); A. Hoekema, in: *The Binary Plant Vector System* (1985) Offsetdrukkerij Ranters, 8.V. Alblasserdam.

Alternatively, to enhance integration into the plant genome, terminal repeats of transposons may be used as borders in conjunction with a transposase. In this situation, expression of the transposase should be inducible, so that once the expression cassette is integrated into the genome, it should be relatively stably integrated and avoid hopping.

The expression cassette will normally be joined to a marker for selection in plant cells. Conveniently, the marker may be resistance to a biocide, particularly an antibiotic, such as Kanamycin, G418, Bleomycin, Hygromycin, Chloramphenicol, or the like. The particular marker employed will be one which will allow for selection of transformed plant cells as compared to plant cells lacking the DNA which has been introduced.

A variety of techniques are available for the introduction of DNA into a plant cell host. These techniques include transformation with Ti-DNA employing *A. tumefaciens* or *A. rhizogenes* as the transforming agent, protoplast fusion, injection, electroporation, DNA particle bombardment, and the like. For transformation with agrobacterium, plasmids can be prepared in *E. coli* which plasmids contain DNA homologous with the Ti-plasmid, particularly T-DNA. The plasmid may be capable of replication in Agrobacterium, by inclusion of a broad spectrum prokaryotic replication system, for example RK290, if it is desired to retain the expression cassette on a independent plasmid rather than having it integrated into the Ti-plasmid. By means of a helper plasmid, the expression cassette may be transferred to the A. tumefaciens and the resulting transformed organism used for transforming plant cells. Conveniently, explants may be cultivated with the A. tumefaciens or A. rhizogenes to allow for transfer of the expression cassette to the plant cells, and the plant cells dispersed in an appropriate selection medium. The Agrobacterium host will contain a plasmid having the vir genes necessary for transfer.

After transformation, the cell tissue (for example protoplasts, explants or cotyledons) is transferred to a regeneration medium, such as Murashige-Skoog (MS) medium for plant tissue and cell culture, for formation of a callus. Cells which have been transformed may be grown into plants in accordance with conventional ways. See, for example, McCormick et al., *Plant Cell Reports* (1986) 5:81–84. The transformed plants may then be analyzed to determine whether the desired gene product is still being produced in all or a portion of the plant cells. After expression of the desired product has been demonstrated in the plant, the plant can be grown, and either pollinated with the same transformed strain or different strains and the resulting hybrid having the desired phenotypic characteristic identified. Two or more generations may be grown to ensure that the subject phenotypic characteristic is stably maintained and inherited.

To identify the desired phenotypic characteristic, transgenic plants which contain and express a given SPS transgene are compared to control plants. Preferably, transgenic plants are selected by measurment of SPS activity in leaf, fruit and/or root. The SPS activity may be periodically measured from various stages of growth through senescence and compared to that of control plants. Plants or plant parts having increased or decreased SPS activity compared to controls at one or more periods are selected. Transgenic plants exhibitng SPS activity from about 1 to 12 fold that of control plants are preferred, with about 1 to 5 fold being more preferred, depending on a desired secondary trait. The activity can be compared to one or more other traits including SPS type, transcription initiation type, translation initiation type, termination region type, transgene copy number, transgene insertion and placement.

When evaluating a phenotypic characteristic associated with SPS activity, the transgenic plants and control plants are preferably grown under growth chamber, greenhouse, open top chamber, and/or field conditions. Identification of a particular phenotypic trait and comparision to controls is based on routine statistical analysis and scoring. Statistical differences between plants lines can be assessed by comparing SPS activity between plant lines within each tissue type expressing SPS. Expression and activity are compared to growth, development and yield parameters which include plant part morphology, color, number, size, dimensions, dry and wet weight, ripening, above- and below-ground biomass ratios, and timing, rates and duration of various stages of growth through senescence, including vegetative growth, fruiting, flowering, and soluble solid content including sucrose, glucose, fructose and starch levels. To identify transgenic plants having other traits, the plants can be tested for photosynthetic and metabolic activity, as well as end-product synthesis. For example, material isolated from transgenic plant cells and plant parts such as leaf, fruit and root are measured for end-products such as starch, sucrose, glucose, fructose, sugar alcohols, and glycine and serine from photorespiratory metabolism following standard protocols. Sweetness based on sugar content, particularly fructose, can be tested as well. For some plants, it may be necessary to modify growth conditions to observe the phenotypic effect. As an example, oxygen, carbon dioxide and light can be controlled and measured in an open gas chamber system, and carbon partitioning measured by $C^{14}$ labeling of carbon dioxide or other metabolic substrates. Carbon partitioning also can be determined in extracts from fruit, leaf and/or root by chromatographic techniques or by Brix using a sugar refractometer. These characteristic also can be compared against or induced by growth conditions which vary gas exchange parameters, light quality and quantity, temperature, substrate and moisture content between lines within each type of growing condition.

The following examples are offered by way of illustration and not by way of limitation.

EXAMPLES

Example 1

Purification of Sucrose Phosphate Synthase of Corn 1.1—Method of determination of enzymatic activity (SPS) During purification SPS activity is followed in 2 ways:
a) either by means of a calorimetric test (Kerr et al., *Planta.*, 1987, 170:515–519) called resorcinol test described below. Sucrose Phosphate Synthase or UDP glucose-D Fructose-Phosphate Glucosyltransferase (EC 2.4.1.14) catalyzes the reaction:

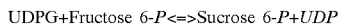
UDPG+Fructose 6-P<=>Sucrose 6-P+UDP

UDPG: Uridine Di-Phospho Glucose
Fructose 6-P or F6P: Fructose 6-Phosphate
Sucrose 6-P: Sucrose 6-Phosphate The sucrose 6-P formed reacts with the resorcinol to give a red-colored compound quantifiable by spectrophotometry at 520 nm (nanometer) (Optical Density (O.D.)=520 nm).

In practice, to 45 μl (microliter) of enzymatic preparation 25 μl of a buffered solution containing the two substrates is added (UDPG 70 mM, F6P 28 mM, $MgCl_2$ 15 mM, HEPES 25 mM pH 7.5). After incubation at 37° C., the reaction is stopped by adding 70 μl of NaOH in solution and heating at 95° C. during 10 min. After cooling, 0.25 ml of a solution 0.1% resorcinol in ethanol 95% is added; then 0.75 ml of HCl 30% is added. The O.D. 520 nM is read after incubation for 8 min at 80° C., and cooling.

b) or by means of a coupled enzymatic system (Harbron et al., *Anal. Biochem.* 1980, 107:56–59) being composed in the following way:

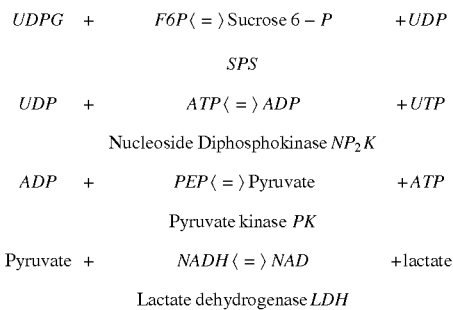

UDPG + F6P⟨ = ⟩Sucrose 6 − P + UDP
                    SPS
UDP + ATP⟨ = ⟩ADP + UTP
        Nucleoside Diphosphokinase $NP_2K$
ADP + PEP⟨ = ⟩Pyruvate + ATP
        Pyruvate kinase PK
Pyruvate + NADH⟨ = ⟩NAD + lactate
        Lactate dehydrogenase LDH The disappearance of the NADH absorption at 340 nm is monitored: 1 mole of NAD formed or 1 mole of NADH consumed corresponds to 1 mole of sucrose 6 P formed.

In practice, in a quartz spectrophotometric tun thermostated at 37° C., the following solution are added.

540 μl of HEPES buffered 50 mM, MgCl$_2$ 10 mM KCl 20 mM pH=7.5,

250 μl of a mixture of substrates PEP (1.6 mM NADH 0.6 mM, ATP 4 mM UDPG 112 mm), 60 μl of an enzyme mixture (LDH 166.7 U/ml PK 333.3 U/ml, NPzK 66.7 U/ml), 100 μl of F6P 112 mM.

After homogenization, 50 μl of the preparation containing SPS is added, the diminution of optical density at 340 nm is added with a spectrophotometer (UVIKON 860, KONTRON instruments). The measure is done with the kinetic of the machine.

1.2 Purification of the SPS (preparation of the immunogen)

1.2.1 Extraction

The starting material for the purification are nature leaves of young corn plants (*Zea mays* L. cv Pioneer 3184), which have been harvested in late morning, cut up, deveined, frozen in liquid nitrogen and stored at −70° C.

250 g of leaves are suspended in 1 liter of 50 mM HEPES 10 mM MgCl$_2$, 1 mM EDTA, 5 mM DTT, pH=7.5 buffer (extraction buffer) which has observed to it 11 g of Polyvinyl-pyrrolidone, nitrogen is bubbled through and the suspension is cooled to 0° C. The leaves are ground, until a homogeneous liquid is obtained. This ground product is filtered, and then centrifuged at 14,000 g for 20 minutes at 4° C. While the bubbling through of nitrogen is maintained, a solution of 50% Poly Ethylene Glycol (PEG 8000 "Breox" at 50% w/v of extraction buffer) is added to the supernatant until a final concentration of PEG of 6% is reached. Then the suspension is cooled at 0° C. After centrifuging at 14,000 g for 20 minutes the supernatant has added to it 50% PEG until a final concentration of PEG of 12% is reached. After a repeated centrifugation, the supernatant is discarded and the residue is solubilized with 60 ml of 50 mM HEPES, 10 mM MgCl$_2$, 1 mM EDTA, 5 mM DTT, 10% Ethylene Glycol (EG), 0.08 M KCl, pH 7.5 buffer (recovery buffer). This solution is clarified by centrifuging at 40,000 g for 10 minutes. The supernatant constitutes the final extract.

1.2.2 Low pressure anion-exchange chromatography: fast-flow DEAE Sepharose exchanger The final extract is chromatographed on a column 25 mm×162 mm of 80 ml of Fast-Flow DEAE Sepharose (Pharmacia) equilibrated with recovery buffer. After washing the column with the same buffer, the proteins adsorbed on the support are eluted by means of a linear gradient with increasing ionic strength between 0.08 M KCl and 0.35 M KCl in the 50 mM HEPES, 10 mM MgCl$_2$, 1 mM EDTA, 5 mM DTT, 10% EG, pH 7.5 buffer (buffer A). The flow rate applied during this experiment is 180 ml/h and chromatography is executed at 4° C.

The SPS activity is eluted at about 0.17 M KCl.

1.2.3 Chromatography on heparin Sepharose

The fractions containing the SPS activity are collected and diluted to one fifth in buffer A, then added to 12 ml of heparin Sepharose previously equilibrated with buffer A. After one hour of incubation with gentle agitation at 4° C., the gel is washed with about 10 volumes of buffer A+0.05 M KCl, then repacked in a chromatography column.

The proteins adsorbed are eluted in an isocratic way by means of a 10 mM CAPS, 10 mM MgCl$_2$, 1 mM EDTA, 5 mM DTT, 10% EG, 0.01% Tween 80, 1 mg/ml heparin, 1% Fructose, 0.25 M KCl, pH 10 buffer, delivered at 60 ml/h. Chromatography is executed at 4° C. The fractions containing the SPS activity are collected (heparin fraction) and preserved on ice until the following purification stage. The enzyme at this stage is stable for a least one week.

The following purification steps are carried out using a system of High Performance Liquid Chromatography (HPLC); the purification is followed by means of a detector fitted with a filter enabling absorbency in the ultra-violet at 280 nm (A280) to be measured. The buffers and the fractions recovered are kept at low temperature.

1.2.4 High performance anion-exchange chromatography: Mono Q

The heparin fraction is diluted by adding one third volume of 20 mM Triethanolamine, 10 mM MgCl$_2$, 1 mM EDTA, 10 mM DTT, 3% EG, 0.3% Tween 80, pH 7.5 buffer (buffer A) and loaded on an FPLC Mono Q HR10/10 column, (10×100 mm Pharmacia) previously equilibrated with the same buffer which has added to it NaCl (final concentration 0.18 M). After the A280 has returned to 0, the proteins adsorbed on the chromatography support are eluted by means of a salt-complex gradient with buffer A (see above) and buffer B (buffer A+NaCl, 1 M) on a Mono Q column as shown below in Table 1.

TABLE 1

Salt Gradient for Mono Q Column

| time (minutes) | % B |
| --- | --- |
| 0 | 18 |
| 0.1 | 24 |
| 15 | 24 |
| 19 | 26 |
| 23 | 26 |
| 33 | 31 |
| 38 | 31 |
| 41 | 100 |
| 43 | 18 |

The flow rate to the Mono Q column is 180 ml/h. The SPS activity is eluted between 0.26 and 0.31 M NaCl. The active fractions are collected together ("Mono Q fraction").

1.2.5 HPLC on Hydroxyapatite

The Mono Q fraction is loaded on an HPLC column of hydroxyapatite 4 mm×75 mm neutralized with 20 mM KH$_2$PO$_4$/K$_2$HPO$_4$, 3% EG, 0.3% Tween 80, 5 mM DTT, pH 7.5 buffer. After the A280 absorbance has returned to 0, the proteins adsorbed to the column are eluted by means of the following phosphate gradient using buffer A (see above) and buffer B (the same as buffer A additionally containing but 500 mM Phosphate of K) as shown below in Table 2.

TABLE 2

Phosphate Gradient for Hydroxyapatite Column

| time (minutes) | % B |
| --- | --- |
| 0 | 2 |
| 5 | 11 |
| 9 | 13 |
| 14 | 13 |
| 29 | 40 |
| 31 | 100 |
| 32 | 100 |
| 35 | 2 |

The flow rate applied to the column is 60 ml/h. At this stage, the phosphate will partially inhibit SPS activity and therefore it is difficult to calculate a specific activity and also a purification factor (see Table 1) at this stage. The SPS activity is eluted under these conditions with about 60 mM phosphate. The active fractions are collected together and constitute the HAC fraction.

1.2.6 HPLC on DEAE 5PW

The HAC fraction is loaded on an anion-exchange HPLC column of Di Ethyl Amino Ethyl type (DEAE-5PW) previously neutralized with a buffer of 20 mM Triethanolamine, 10 mM MgCl$_2$, 1 mM EDTA, 3% EG, 2.5 mM DTT, 2% betaine, pH 7.5 buffer (buffer A)+0.15 M NaCl.

After the A280 absorbance has returned to 0, the proteins adsorbed to the column are eluted by means of the following NaCl gradient using buffer A (see above) and buffer B (the same as buffer A but additionally containing 1 M NaCl) as shown below in Table 3.

TABLE 3

Salt Gradient for DEAE Column

| time (minutes) | % B |
|---|---|
| 0 | 15 |
| 0.1 | 20 |
| 5 | 20 |
| 22 | 35 |
| 27 | 35 |
| 30 | 100 |
| 31 | 15 |

The flow rate applied to the column is 60 ml/h. The SPS activity is eluted with about 0.3M NaCl.

1.2.7 Preparation of the final preparation: concentration

The final preparation is concentrated by HPLC chromatography on a Mono Q HR5/5 exchanger (5×50 mm, Pharmacia) and rapid elution. The DEAE 5PW fraction (or the G200 fraction) is diluted to two thirds with buffer A (see 1.2.6) and loaded on the column which previously has been neutralized with buffer A+0.18 M NaCl. The following gradient is then applied on the column using buffer A and B (see 1.2.6) as shown below in Table 4.

TABLE 4

Gradient for Concentration

| time (minutes) | % B |
|---|---|
| 0 | 18 |
| 10 | 40 |
| 12 | 100 |
| 13 | 18 |

The flow rate applied to the column is 60 ml/h. The SPS activity is eluted with about 0.3 M NaCl. The final preparation is stored at −20° C. until used.

The results obtained at the various purification stages in terms of quantities of proteins recovered and of SPS activity are summarized in Table 5 below.

TABLE 5

Purification of Corn SPS

| | Concentration of proteins (mg/ml) | Volume (ml) | sA[1] (ml) | pF[2] | Y[3] (%) |
|---|---|---|---|---|---|
| Ground product | 1 | 1000 | 0.05 | 0 | 100 |
| Final Extract | 4 < < 8 | 60 | 0.30 | 6 | 144 |
| DEAE FF fraction | 0.4 < < 0.8 | 70 | 3 | 60 | 168 |
| Heparin fraction | 0.2 < < 0.4 | 25 | 9 | 180 | 90 |
| Mono Q fraction | (0.02)[4] | 30 | —[5] | —[5] | —[5] |
| HAC fraction | (0.03)[4] | 8 | —[5] | —[5] | —[5] |
| Final preparation | 0.05 | 2 | 25 | 500 | 5 |

[1]sA = Specific enzymatic activity: 1 U corresponds to 1 μm of sucrose formed per minute per mg of protein at 37° C. The measurement of the quantity of proteins is carried out using the Bradford method. As Tween interferes enormously with this method, it is not possible to determine the proteins and then to calculate an sA at the level of the stages containing one. Furthermore, as phosphate is an inhibitor of SPS activity, the determination during the HAC stage gives an underestimated result.
[2]pF = Purification factor
[3]Y = Yield. The increasing yield during the initial stages of purification can be explained by the elimination, during purification, of certain inhibitors of SPS activity.
[4]( ) = approximate value
[5]— = not determined An SDS-PAGE profile at various stages of the purification process and the quality of the final preparation is given in FIG. 1. The 120, 95 and 35 kd proteins are correlated to the SPS activity. The 35 and 95 kd proteins are very likely breakdown products of the 120 kd protein as it can be shown by the nucleotidic sequence coding for the SPS protein. Furthermore, the antibodies directed against the 35 and 95 kd proteins also recognize the protein 120 kd in immunodetection after membrane transfer, which demonstrates an antigenic identity between these three proteins (see below). It must be pointed out, however, that the addition of protease inhibitors in the buffers during purification has not enabled us to obtain a single 120 kd protein.

Gel permeation chromatographies were carried out in order to determine the apparent molecular weight of the native SPS protein. Briefly, the HAC fraction was concentrated by HPLC chromatography on a Mono Q HR 5/5 inchanger (see 1.2.7). The active fractions were collected together (about 2 ml) and loaded on an G 200 column previously washed with a buffer containing 20 mM triethanolamine, 10 mM MgCl$_2$, 1 mM EDTA, 3% E.G., 2.5 mM DTT, 2% betain, 0,3 M NaCl pH 7.5. The SPS activity was eluted with a major protein peak corresponding to an apparent mass of 270–280 kda which is in agreement with the results obtained by Harbron et al. (*Arch. Biochem. Biophys.*, 1981, 212:237–246) with the spinach SPS. It can be noted that the chromatography on a TS lambda 60000 permeation column lead to the elution of the SPS activity at a retention time corresponding to an apparent mass of 440 kda which is close to the value obtained by Doehlert and Huber (*Plant Physiol.*, 1983, 73:989–994) with the spinach SPS, using an AcA34 permeation column.

The SPS protein seems therefore to be a di or tetrameric protein having as the basic sub-unit a 120 kda protein (homodimeric or homo-tetrameric). The results of SDS page 2 0 analysis at various stages of purification are shown in FIG. 1. The bands of proteins visible at about 120 kd (1), 95 kd (2) and 35 kd (3) are correlated, during the chromatography stages, with the appearance of SPS activity in the respective fractions.

Example 2

Process for the Preparation of Monoclonal Antibodies Directed Against SPS 2.1 Immunizations BALB/c mice were immunized by subcutaneous injection (pads and paws) according to the following methodology:

Day 0 injection of about 5 micrograms of proteins (or about 0.3 U SPS per mouse): Mono Q pool emulsified volume for volume with Freund's Complete Adjuvant (FCA).

Day 14 injection of about 5 micrograms of proteins (or about 0.3 U SPS per mouse): Mono Q pool emulsified volume for volume with Freund's Incomplete Adjuvant (FIA).

Day 27 Idem D14

Day 0+60 injection of about 20 micrograms of proteins: final pool in FIA

Day 0+90 injection of about 12 micrograms of proteins: final pool in FIA

Day 0+135 injection by intravenous route (IV) in the tail of about 20 micrograms of proteins: final pool.

Fusion is achieved 3 days after the IV immunization.

The sera were removed at D34, D61, D98 and D159 in order to measure the immune response (see screening).

2.1.1 Screening method

Two methods were used to detect antibodies specific to the SPS used for immunizations:

detection method of antibodies inhibiting the SPS activity
detection method of antibodies directed against the SPS (inhibiting or not).

a) Detection method of antibodies inhibiting the SPS activity

This method of screening allows the detection of antibodies which interfere with the active site of the SPS or on a site close to the latter, and therefore prevent the access of substrates. In practice, 70 µl of serum or of supernatant of hybridoma culture diluted in a suitable way was mixed with 70 µl of SPS preparation (Heparin fraction). After one hour of incubation at ambient temperature, the residual SPS activity was determined by coupled enzymatic determination (see 1.1). The results are expressed as a percentage of inhibition as compared to the same SPS preparation treated in the same way but without antibodies.

b) Detection method of antibodies directed against SPS (inhibiting or not)

This method is based on the precipitation of the antibody-SPS complex by goat anti-mouse IgG coupled to sepharose beads (GAM sepharose). In practice, 60 µl of serum or supernatant of hybridoma culture diluted in any suitable manner were added to 60 µl of SPS preparation (Heparin fraction). After 2 hours of incubation at ambient temperature, the mixture was added to 50 µl of 25% GAM-Sepharose previously washed three times with a buffer of 50 mM HEPES, 10 mM $MgCl_2$, 1 mM EDTA, 10% EG, 5 mM DTT, pH 7.5. The mixture was incubated overnight at 4° C. with strong agitation. After centrifuging the mixture for 5 minutes at 3000 rpm, the residual SPS activity in the supernatant was determined by coupled enzymatic determination (see 1.1). The results are expressed as a percentage of precipitation (% prec.) as compared to the same SPS preparation treated in the same way without antibodies.

2.1.2 Results mice were immunized according to the protocol described previously. The following table gives the results of the precipitation determinations carried out with the heteroantisera of the 10 mice on D159. The sera are diluted to one two-hundredth.

TABLE 6

Percentage Precipitation of Antibody-SPS Complex

| Mouse | 1 | 2 | 3 | 4 | 5 | 6 | 7 | 8 | 9 | 10 |
|---|---|---|---|---|---|---|---|---|---|---|
| % Prec. | 45 | 22 | 32 | 64 | 36 | 30 | 22 | 16 | 39 | 37 |

Additional dilutions of the serum of mouse 4 give the following results:

TABLE 7

Percentage Precipitation of Serial Dilutions of Mouse 4 Serum

| Dilution | % Precipitation |
|---|---|
| 1/200 | 67 |
| 1/400 | 48 |
| 1/600 | 29 |
| 1/1000 | 20 |

The spleens of mice 1 and 4 were used for the fusion with myeloma cells.

2.2 Cellular fusion

The splenocytes of the mice were fused with myeloma cells of SP2/0-Ag14 mice according to a ratio of 2:1 in the presence of 45% polyethylene glycol 1500. The selection of the hybridomas was effected by adding hypoxanthine and azaserine to the culture medium 24 and 48 hours after fusion.

The hybridomas were cloned and sub-cloned by the method of limited dilution.

2.2.1 Results of the screening of hybrids and clones

Results from screening of hybrids, clones and sub-clones are shown below in Table 8.

TABLE 8

Hybrid, Clone and Sub-clone Screening

| Hybrids | |
|---|---|
| Mouse 4 (SPA fusion) | Mouse 1 (SPB fusion) |
| 2 positive hybrids out of 45 | 6 positive hybrids out of 52 |
| SPA2: 38% prec. | SPB3: 17% prec. |
| SPA19: 7% prec. | SPB5: 67% prec. |
| | SPB8: 53% prec. |
| | SPB13: 68% prec. |
| | SPB25: 13% prec. |
| | SPB34: 17% prec. |

| Clones | |
|---|---|
| SPA fusion | SPB fusion |
| 2 clones retained out of 36 | 7 clones retained out of 46 |
| SPA2-2: 85% prec. | SPB3-2: 19% prec. |
| SPA19-7: 8% prec. | SPB5-1: 76% prec. |
| | SPB5-2: 71% prec. |
| | SPB5-3: 45% prec. |
| | SPB5-4: 24% prec. |
| | SPB13-1: 79% prec. |
| | SPB13-2: 53% prec. |

| Sub-Clones | |
|---|---|
| SPA fusion | SPB fusion |
| sub-clones retained out of 48 | sub-clones retained out of 72 |
| SPA2-3: 60% prec. | SPB3-2-19: 21% prec. |
| SPA2-2-33: 33% prec. | SPBS-2-10: 86% prec. |

TABLE 8-continued

Hybrid, Clone and Sub-clone Screening

| | |
|---|---|
| SPA2-2-25: 92% prec. | SPBS-4-2: 46% prec. |
| | SPB13-1-7: 87% prec. |
| | SPB13-2-2: 93% prec. |

2.2.2 Production of anti-SPS monoclonal antibodies

The hydridomas were injected by the intra-peritoneal route into female BALB/c mice previously treated with pristane. The monoclonal antibodies were partially purified from asertes fluids precipitated with 18% sodium sulphate. The proteins so precipitated were dissolved then dialyzed against PBS (F18).

2.2.3 Characterization of anti-SPS monoclonal antibodies a) Typing

The typing was done using an ELISA test. Anti-IgG rabbit and anti-IgM mouse antibodies (Zymed) were fixed at the bottom of the wells of a 96-well plate. After one night at ambient temperature the unoccupied sites were saturated with a solution of 3% bovine serum albumin in PBS. After one hour of incubation at 37° C. and several washes, the various F18's were deposited in the wells. After incubation and several washes, goat or rabbit antibodies, anti-class and anti-sub class mouse immunoglobulins linked with peroxidase, were added. After one hour at 37° C., the antibody type was identified using an $H_2O_2$/ABTS system. All the anti-SPS monoclonal antibodies were found to be of $IgG_1$ type.

b) Inhibition of SPS activity

The determination of the capacity of the antibodies to inhibit the SPS activity was carried out by the technique mentioned previously (see 2.1.1 a) using F18's. The results are shown below in Table 9.

TABLE 9

Inhibition of SPS Activity

| Antibody | Concentration of antibodies (mg/ml) | % Inhibition |
|---|---|---|
| SPA2-2-3 | 50 | 0 |
| SPA2-2-22 | 50 | 0 |
| SPA2-2-25 | 50 | 0 |
| SPA3-2-19 | 50 | 0 |
| SPA5-2-10 | 50 | 0 |
| SPA5-4-2 | 50 | 0 |
| SPA13-1-7 | 50 | 50 |
| | 25 | 55 |
| | 5 | 25 |
| | 2.5 | 10 |
| | 1 | 2.1 |
| SPB13-2-2 | 50 | 60.1 |
| | 25 | 59.1 |
| | 5 | 33.8 |
| | 2.5 | 14.2 |
| | 1 | 8.7 | c) Immuno-precipitation of the SPS activity

The determination of the ability of the antibodies to immunoprecipitate the SPS activity was carried out by the technique mentioned previously (see 2.1,1 b) using F18's. The results are shown below in Table 10.

TABLE 10

Immunoprecipitation of SPS Activity

| Antibody | Concentration of antibodies (mg/ml) | % Precipitation |
|---|---|---|
| SPA2-2-3 | 50 | 95 |
| | 25 | 92 |
| | 5 | 80 |
| | 2.5 | 40 |
| | 1 | 20 |
| SPA2-2-22 | 50 | 95.7 |
| | 25 | 95 |
| | 10 | 51 |
| | 5 | 48.2 |
| | 2.5 | 25 |
| | 1 | 10.1 |
| SPA2-2-25 | 50 | 91.3 |
| | 25 | 95.3 |
| | 5 | 90.4 |
| | 2.5 | 22.8 |
| | 1 | 12.5 |
| SPB3-2-19 | 50 | 95 |
| | 25 | 95 |
| | 5 | 27.8 |
| | 2.5 | 17.8 |
| | 1 | 9.3 |
| SPB5-2-10 | 50 | 95 |
| | 25 | 95 |
| | 5 | 81.1 |
| | 2.5 | 41.4 |
| | 1 | 22.6 |
| SPB5-4-2 | 50 | 95 |
| | 25 | 95 |
| | 5 | 86.1 |
| | 2.5 | 57.2 |
| | 1 | 26.1 |
| SPB13-1-7 | 50 | 95 |
| | 25 | 95 |
| | 10 | 65.4 |
| | 5 | 48.1 |
| | 2.5 | 15 |
| | 1 | 10 |
| SPB13-2-2 | 50 | 95 |
| | 25 | 95 |
| | 5 | 71.8 |
| | 2.5 | 43.5 |

Example 3

Use of the Monoclonal Antibodies for the Characterization and Purification of SPS 3.1 Characterization of Corn SPS This characterization was carried out with SPB3-2-19 and SPB13-2-2 antibodies by the technique of immuno-detection after transfer of the proteins from an electrophoresis gel under denaturing conditions (SDS-PAGE) on nitrocellulose membrane (Western). After electrophoretic separation in a 12.5% acrylamide gel (Nature 277 (1970) 680–685), the proteins were transferred onto a 0.22 μm nitrocellulose membrane (Schleicher and Schuell). The buffer was a standard electrophoresis buffer (3.03 g/l. TRIS base, 14.4 g/l. Glycine, 0.1% SDS, pH 8.3, 20% methanol).

Figure 2:
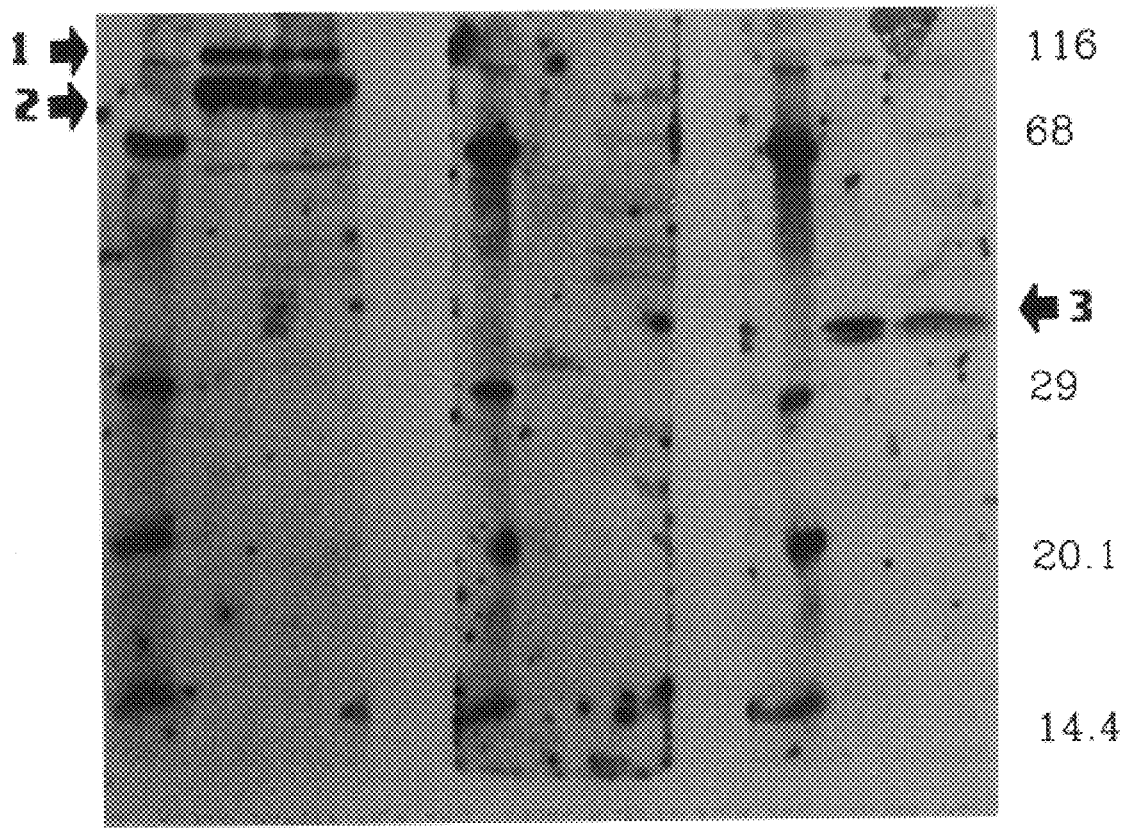
FIGS. 2A–2C shows the results of a Western analysis of SPS using monoclonal antibodies.

After transfer, the membrane was put in a blocking bath (0.5% Casein in PBS). After one hour at 37° C. under gentle agitation, the membrane was washed 3 to 4 times in a washing buffer (0.1% Casein, 0.5% Tween 20, in PBS) then incubated with a solution of 10 micrograms/ml of the monoclonal antibody to be tested. A part of the membrane was incubated in parallel with a non-immune antibody (negative control). After one hour of incubation at ambient temperature followed by 9 or 10 washes, the membrane was incubated in the presence of an anti-mouse antibody labelled with $^{125}I$ diluted in a washing buffer (50,000 cpm per cm$^2$ of membrane). After one hour of incubation at ambient temperature followed by 9 or 10 washes, the membrane was dried, then autoradiographed (X-OMAT AR Kodak film and Crone XTRA Life Dupont amplifying screen). The results of the autoradiography are shown in FIG. 2. In the autoradiograph, a strong signal is observed at the protein bands 120 kd, 95 kd and 35 kd which correlates with the previous results (see first part).

3.2 Purification of Sucrose Phosphate Synthase by Immunoaffinity Chromatography

A methodology for the purification of corn Sucrose Phosphate Synthase on an immunoaffinity support has been perfected in order to increase the quantity of protein recovered while reducing the number of purification stages and to obtain quantities sufficient for protein sequencing.

3.2.1 Preparation of the immuno-adsorbent

The F18 (see 2.2.2) corresponding to the SPB13-1-7 antibody or to the SPB13-2-2 antibody were mixed with activated CH-Sepharose, (1 mg of antibody per ml of gel). After incubation for 2 hours at ambient temperature, the sites not occupied by the antibodies were saturated with IM ethanolamine, pH 9. The support was then washed alternately with zero 0.1M acetate 0.5 M NaCl, pH 4 buffer and 0.1 M TRIS 0.5 M NaCl, pH 8 buffer. The immunoaffinity support thus prepared was preserved at 4° C. in a 50 mM HEPES, 10 mM MgCl$_2$, 1 mM EDTA, 1 mM PMSF, zero 0.01% sodium nitride (azide), pH 7.5 buffer.

3.2.2 Immunoaffinity Chromatography

50% PEG was added to the Heparin fraction of SPS (see 1.2.3.) to give a final concentration of PEG of 20%. After incubation for 30 minutes at 4° C. with gentle agitation, the mixture was centrifuged at 1600 g for 30 minutes. The protein deposit was taken up in half of the initial volume with the 50 mNM HEPES, 10 mM MgCl$_2$, 1 mM EDTA, 10% ethylene glycol, pH 7.5 buffer. This stage allows the previous buffer, which is incompatible with the immunoaffinity chromatography, step to be eliminated, and the proteins to be concentrated. The yield of SPS activity was from 80 to 90%.

The solution obtained was applied with a flow rate of 0.1 ml/min over 1 ml of immunoaffinity support packed in a column and on which had been fixed an antibody not directed against the SPS (activated CNBr-Sepharose, on which an antineomycin antibody is fixed). This first stage allows the elimination of certain contaminants which are fixed nonspecifically on the chromatography support. The effluent of the non-specific column was in turn applied to the anti-SPS immunoaffinity support (2 ml in an 11×20 mm column) with a flow rate of 0.1 ml/min. These two stages were carried out at laboratory temperature. The column was washed with 10 ml of load buffer and then with a washing buffer (load buffer with the addition of 0.25 M NaCl and 0.3% Tween 20) until absorbency in ultra-violet at 280 nm was close to base level. The proteins adsorbed on the support were eluted with a solution of 50 mM triethylamine, pH 11. This elution was carried out at 4° C. and the immunoaffinity column was reversed to obtain an optimum yield. The SDS-PAGE profile of the final preparation obtained corresponds to that obtained using the standard protocol (see 1). It must be noted that the elution method of the proteins adsorbed on the immunoaffinity support irreversibly destroys the SPS activity but the recovery yield of the eluted SPS proteins is optimal compared to tests carried out in native elution conditions. The eluate of the immunoaffinity column was desalted using a Sephadex G25 column, against a 0.14% Glycerol, 0.07% 2-mercapto-ethanol, 0.04% SDS, 0.9 mM TRIS pH 6.8 buffer (electrophoresis buffer in reducing conditions diluted 70 times). After desalination, the protein preparation was concentrated 70 times with a concentrator under vacuum and the SPS proteins were purified by SDS-PAGE (see below).

Example 4

Partial Sequencing of SPS Polypeptides 4.1 Purification of SPS Polypeptides for Sequencing Samples of a purified protein preparation obtained as described in Example 3.2.2. were subjected to preparative SDS-PAGE. After electrophoresis, the protein bands were visualized with KCl treatment as described by Bergman and Joernvall (*Eur. Biochem.* (1978) 169:9–12) and the bands observed at 90 kd and 30 kd were excised. The proteins from these gel fragments were electroeluted using an Electrophoretic Concentrator according to manufacturer's instructions (ISCO; Lincoln, Nebr.) in 4 mM sodium acetate, pH8. After electroelution, protein yields were quantitated by comparison to a bovine serum albumin (BSA) standard on a Coomassie Blue-stained gel. Approximately 30 mg of the 30 kd protein and 75 μg of the 90 kd protein were obtained.

4.2 Tryptic Digestion and Protein Sequencing of SPS Polypeptides

The proteins were concentrated by acetone precipitation, and resuspended in 50 mM ammonium carbonate buffer, pH 8. Tryptic digestion and HPLC purification were performed as described by Sturm and Chrispeels (*Biol. Chem.* (1987) 262:13392–13403). Briefly, digestion was performed by addition of trypsin (5% of SPS protein), and incubation for two hours at 37° C. The digestion was then repeated. The proteins were concentrated by lyophilization and resuspended in 50 mM sodium phosphate buffer, pH 2.2. This mixture was subjected to reverse phase HPLC separation by application to a C18 column in phosphate buffer. Elution was performed using an increasing gradient of acetonitrile. Eluted material from the phosphate buffer/acetonitrile gradient was monitored at 214 nm. The fractions corresponding to peaks of absorbance at 214 nm were collected, lyophilized, resuspended in 0.1% trifluoroacetic acid, reapplied to the C18 column (equilibrated with 0.1% trifluoroacetic acid), and eluted using an acetonitrile gradient. Eluted material from the trifluoroacetic acid/acetonitrile gradient was monitored at 214 nm. The fractions corresponding to peaks of absorbance at 214 nm were collected, lyophilized, and subjected to standard Edman degradation protein sequencing on an automated protein sequencer (Applied Biosystems Foster City, Calif.). Sequences of five peptides were obtained. See FIG. 3 (SEQ ID NOS: 1–5).

Example 5

Isolation and Assembly of a Full-Length cDNA for SPS 5.1 RNA Isolation from Corn Leaf Total RNA was isolated from corn leaves (see 1.2.1.) according to the method of Turpen and Griffith (*Biotechniques* (1986) 4:11–15). Briefly, 250 gm of material was homogenized in 4M guanidine thiocyanate and 2% sarcosyl. The mixture was then centrifuged and the cleared supernatant was layered into a 5.7 M CsCl cushion and centrifuged for 5.5 hours at 50,000 rpm. The RNA pellet was dissolved in water, extracted with phenol and chloroform, and precipitated with ethanol. The resulting pellet was resuspended in water. The final yield from the RNA isolation step was quantitated by UV spectrophotometry.

5.2 Poly(A) RNA Isolation

A saturated suspension of cellulose powder/water was added to the RNA/water mixture obtained in 5.1, at 10% of the total volume, to remove residual polysaccharides. After centrifugation, the supernatant, containing the RNA, was applied to an oligo(dT)-cellulose column as described by Maniatis et al. (*Molecular Cloning: A Laboratory Manual*, (1982) Cold Spring Harbor, N.Y.). The fraction containing the poly(A)+RNA was then reapplied to the column. The eluted fraction containing the poly(A)+RNA was extracted with 2 0 phenol, and the RNA was precipitated with ethanol. Analysis by gel electrophoresis showed complete absence of ribosomal RNA.

5.3 Construction of Total Corn Leaf Library cDNA synthesis was performed according to the manufacturer's instructions (RiboClone cDNA Synthesis System by Promega, Madison, Wis.), using five μg of poly(A)+RNA as template, except that M-MLV reverse transcriptase (BRL; Bethesda, Md.) was substituted for AMV reverse transcriptase. EcoRI linkers were added to the blunt-ended cDNA, and the resulting fragments were cloned into an expression vector (LambdaZAP, Stratagene; La Jolla, Calif.) according to the manufacturer's instructions. The resulting library contained approximately $1.5 \times 10^6$ transformants.

5.4 PCR Generation of a Partial SPS cDNA Probe

Using the sequence information from the peptides of Example 4 (SEQ ID NOS: 8–9) and the polymerase chain reaction (PCR), a 1200 bp SPS cDNA fragment was generated. Total corn leaf cDNA (5.3.) was used as a template, and degenerate oligonucleotides (SEQ ID NOS: 10–13), designed from two peptide sequences of the 30 kd and 90 kd SPS polypeptides, were used as primers. These primer sets were designated as CD3 (SEQ ID NOS: 10–11) and CD4 (SEQ ID NOS: 12–13). See FIG. 4. PCR was carried out, according to the manufacturer's instructions (GeneAmp DNA Amplification Reagent Kit and DNA Thermal Cycler of Perkin Elmer Cetus; Norwalk, Conn.) except that the reaction was carried out for 30 cycles, and the annealing steps were programmed to be at 50° C. for 1 minute. The PCR reactions were analyzed by agarose gel electrophoresis. Use of the correct set of primers, CD3, resulted in a 1200 bp band being generated by the PCR reaction. PCR using the other set of primers, CD4, gave no specific signals. See FIG. 5. Southern analysis (see FIG. 5) confirmed that the PCR band was not an artifact. The probe 4K5 (SEQ ID NO: 14) was used because the corresponding sequence of the probe was predicted to be within the 1200 bp fragment if the fragment corresponded to the SPS sequence. The probe hybridized to the 1200 bp band generated by PCR using the primer set CD3 but not to PCR products generated by the primer set CD4. See FIG. 5.

5.5 Isolation of SPS Bacteriophage Lambda cDNA Clones

The 1200 bp PCR-generated fragment was labeled with $^{32}$P (as per the Random Primed DNA Labeling Kit, Boehringer Mannheim, Indianapolis, Ind.) and used as a probe to screen approximately 250,000 plaques of the cDNA library (5.3.). The inserts of the positive clones were analyzed by restriction analysis with EcoRI, and the clones with the longest inserts, SPS#3 and SPS#18, were selected for further analysis. See FIG. 6. A 0.4 kb HindIII/EcoRI fragment from the 5' end of SPS#3 was isolated, then labeled with $^{32}$p by random priming (Random Primed DNA Labeling Kit) and used as a probe to re-screen the library. Another clone, designated SPS#61, which extends further upstream than SPS#3, was isolated. See FIG. 6. DNA sequencing indicated that the 5' end of the SPS reading frame was not reached.

To isolate cDNA clones that included more of the 5' region than SPS#3 or SPS#61, a new cDNA library was prepared, as per Example 5.3., (RiboClone cDNA Synthesis System by Promega; Madison, Wis.) using M-MLV reverse transcriptase instead of AMV reverse transcriptase. However, instead of using oligo (dT) as a primer, a synthetic 17 bp primer, 23B, derived from the 5' sequence of the SPS#61 clone, was used (see FIG. 6). This resulted in cDNAs that contain only regions upstream of the SPS#61 5' region. The library was screened with the $^{32}$P-labeled EcoRI insert from SPS#61, and 16 positive clones were obtained. The clones with the longest inserts, SPS#77 and SPS#90, were selected for further analysis. DNA sequencing of SPS#77 and SPS#90 showed that the region of overlap (greater than 100 bp) with SPS#61 was identical in all clones, and that both extended further upstream into the 5' region. See FIG. 6.

PCR was carried out using single-stranded cDNA (from a reverse transcriptase reaction corn leaf RNA (5.2.) primed with oligo (dT) as described above) as template and primers selected from the SPS#90 and SPS#3 sequences, confirmed that SPS#90 and SPS#3 originate from the same mRNA transcript. The fragment resulting from this PCR reaction was 750 bp in length, consistent with the size predicted from the DNA sequence. The 750 bp fragment was subcloned into a Bluescript-derived vector as a SalI/HindIII fragment. Four of the resulting subclones were partially sequenced, and the sequence obtained matched the existing DNA sequence.

5.6 Assembly of the SPS Reading Frame

Both DNA strands of SPS#90, SPS#61, and SPS#3 were sequenced, using the method of Sanger et al. (*PNAS* (1977) 74:5463–5467). All three sequences can be combined to form one contiguous sequence of 3509 bp. See FIG. 7 (SEQ ID NO: 6). Primer extension experiments using corn leaf poly(A) RNA and an antisense primer showed that the 5' end of our DNA sequence represents sequences from the actual 5' end of the SPS in RNA. In the SPS reading frame, as defined by the five peptide sequences (SEQ ID. NOS.: 1–5 respectively) (see FIG. 3), the first methionine codons are located at bp 112 and bp 250. See FIG. 7 (SEQ ID NO: 6). The codon at bp 112 is similar to the consensus eukaryotic translational start site (Kozak, *Cell* (1986) 44:283–292) and is located 54 bp downstream of a TAG stop codon (bp 58). It is proposed that this codon represents the translational start of the SPS polypeptide in vivo. After a 1068 codon reading frame, translation is stopped by TGA. The following 193 bp contain the 3' untranslated region including a poly(A) addition signal, AAATAAA.

The full-length SPS coding region can be assembled by combining the 529 bp BamHI/HindIII fragment of SPS#90, the 705 bp HindIII fragment of SPS#61 and the 2162 bp HindIII/EcoRI fragment from SPS#3 (see FIG. 6).

Example 6

Figure 8:
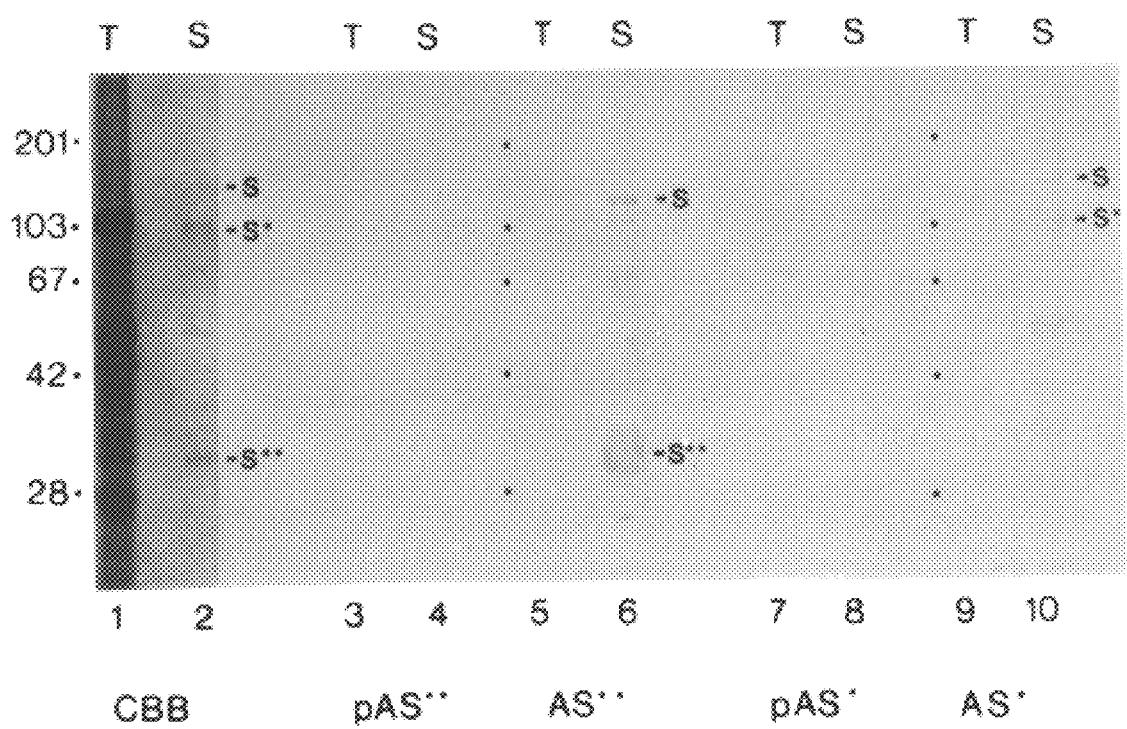
FIG. 8 shows Western blots demonstrating the characteristics of rabbit SPS 90 and SPS 30 antisera. The abbreviations used are: pAS=preimmune serum, SPS 30 rabbit; AS=immune serum anti-SPS 90. Molecular weight markers at left, where indicated. S=SPS 120 kd polypeptide; S*=SPS 90 kd polypeptide; S**=SPS 30 kd polypeptide.

Detection of SPS Polypeptides by Specific Antisera 6.1 Preparation of Antibodies to SPS Samples of purified protein preparations obtained by the method described in 3.2.2. were subjected to SDS-PAGE electrophoresis. The proteins in the gel were fixed and stained. The bands corresponding to the 90 kd and 30 kd polypeptides were excised. Using this material, polyclonal antisera were raised in rabbits by conventional procedures. Western analysis (as described by Oberfelder, *Focus* (1989) 11(1):1–5) showed that the antibodies isolated from the rabbit immunized with SPS 30 recognized the bands corresponding to the SPS#30 and SPS#120 peptides on a SDS PAGE gel, and that the antibodies isolated from the rabbit immunized with SPS#90 recognized the bands corresponding to the SPS#90 and SPS#120 polypeptides (see FIG. 8).

6.2 Immunological Localization of SPS in the Corn Plant

Figure 9A:
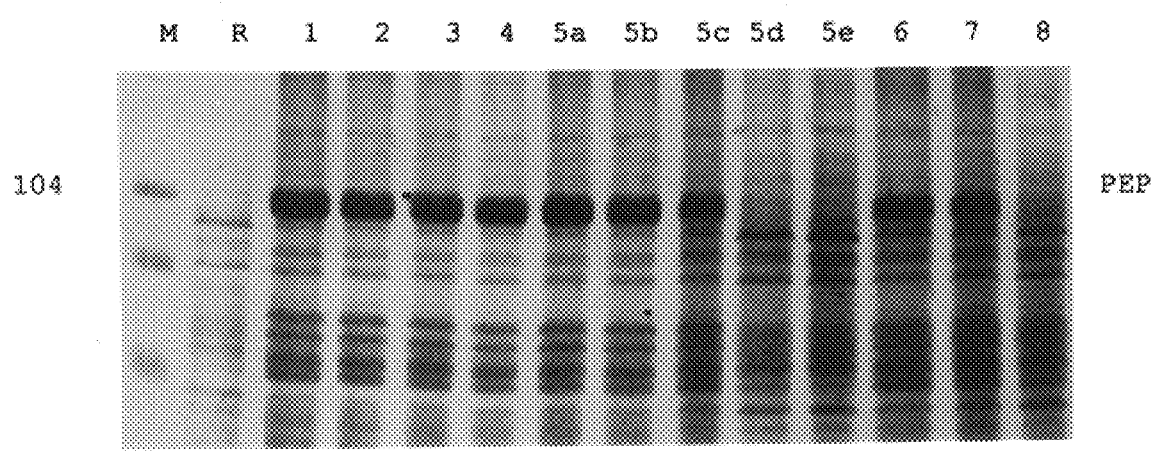
FIGS. 9A–9B show analysis of protein from a 30-day old corn plant.
Figure 9B:
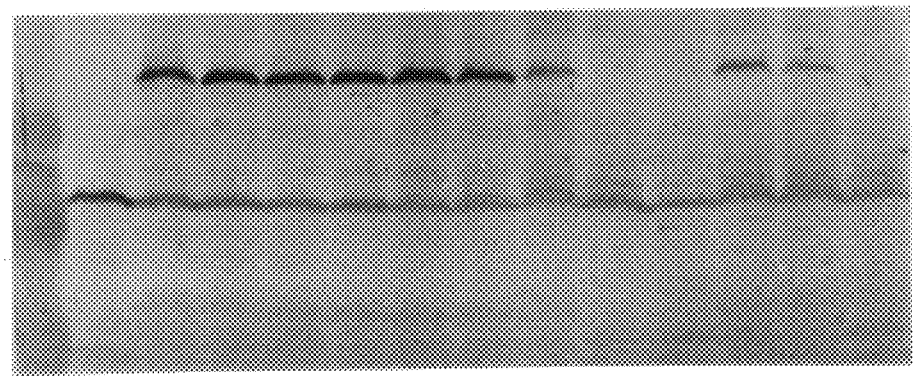

Total proteins were extracted from leaves of a 30 day-old corn plant, harvested at 11:00 am, by boiling in SDS buffer. The protein extracts were loaded on duplicate SDS-PAGE gels. One gel was stained with Coomassie Blue, while the other was subjected to Western analysis, using a mixture of SPS#30 and SPS#90 antisera as probe. See FIG. 9. The prominent bands appearing on the Coomassie Blue-stained gel were identified as phosphoenolpyruvate carboxylase (PEPcase), an enzyme involved in C4 photosynthesis. The Western blot showed the presence of the SPS band. The SPS protein pattern was very similar to the PEPcase protein pattern: not present in roots, nor present in the section of leaf closest to the stem, nor present in very young leaves. This pattern corresponds with expression associated with photosynthesis, and is the pattern expected for SPS.

Example 7

Construction of Expression Construct Plasmids 7.1 Construction of the full-length SPS reading frame Clone SPS#90 was digested with HindIII and ligated with the 705 bp HindIII fragment from clone SPS#61 to create a plasmid containing the 5' end of the SPS coding region. The resulting plasmid was digested with BamHI and partially digested with HindIII, resulting in a 1340 bp BamHI/HindIII fragment containing the 5' end of the coding region. The 3' end of the SPS coding region was obtained by digestion of SPS#3 with EcoRI and partial digestion with HindIII, resulting in a 2162 bp HindIII/EcoRI fragment. This 2162 bp HindIII/EcoRI fragment, carrying the 3' end, was ligated with the 1340 BamHI/EcoRI fragment carrying the 5' end into a BamHI/EcoRI-digested pUC-derivative plasmid Bluescript, to create a plasmid carrying the entire 3403 bp SPS coding region and 3' untranslated transcription termination region.

7.2 Expression of SPS in *E. coli*

When cloning the 3403 bp BamHI/EcoRI SPS fragment into the plasmid Bluescript SK (Stratagene, La Jolla, Calif.), a translational fusion between the plasmid coded lacZ sequence and the SPS reading frame was created. The resulting fusion protein contains 30 N-terminal amino acids from the β-lactosidase and the complete SPS polypeptide. The fusion protein was expressed in *E. coli* under the Bluescribe plasmid lacZ promoter. Preparation of total protein followed by Western analysis using anti-SPS antisera (see 6.1.) shows a band comigrating with native plant SPS. For the SPS activity test, the *E. coli* cells containing the SPS expression construct as described were opened with lysozyme and sonication. Soluble protein was desalted by a Sephadex G-25 column. This protein extract was assayed for SPS activity analogous to the method described in 1.1.a., except that the reagent anthrone was used instead of resorcinol (Handel, *Analytical Biochemistry*, (1968) 22:280–283). This test showed that the SPS protein, expressed from the cDNA in *E. coli* does have SPS enzyme activity. By comparison to native plant enzyme it seems to have the same specific activity.

7.3. Construction of the Tobacco Small Subunit (SSU) Promoter-Transcriptional Fusions The SPS coding region can be conveniently cloned as a BamHI/EcoRI (bp 106–bp 3506) fragment 3' of a tobacco small subunit promoter. A SSU promoter for expression of the SPS coding region, was prepared as follows. The SSU promoter region from pCGN627 (described below) was opened by KpnI and the 3' overhang removed. After EcoRI digestion, the 3403 bp BamHI (filled in) EcoRI SPS cDNA fragment (see, Example 7.1.) was inserted.

After the SPS coding region was ligated into the SSU promoter, the SSU/SPS region was ligated into a binary vector and integrated into a plant genome via Agrobacterium tumefaciens-mediated transformation. (The SPS region carries its own transcription termination region in the cDNA sequence). Insertion of the SSU/SPS construct into the binary vector pCGN1557 resulted in pCGN3812.

pCGN627

The 3.4 kb EcoRI fragment of TSSU3-8 (O'Neal et al., *Nucleic Acids Res.* (1987) 15:9661–8677), containing the small subunit promoter region, was cloned into the EcoRI site of M13mp18 (Yanisch-Perron et al, *Gene* (1985) 53:103–119) to yield an M13 clone 8B. Single-stranded DNA was used as a template to extend the oligonucleotide primer "Probe 1" (O'Neal et al., *Nucleic Acids Research* (1987) 15:8661–8677) using the Klenow fragment of DNA polymerase I. Extension products were treated with mung bean nuclease and then digested with HindIII to yield a 1450 bp fragment containing the SSU promoter region. The fragment was cloned into HindIII-SmaI-digested pUC13 (Yanisch-Perron et al., *Gene* (1985) 53:103–119) to yield pCGN625. pCG2J625 was digested with HindIII, the ends blunted with Klenow, and the digested plasmid re-digested with EcoRI. The EcoRI/blunted-HindIII fragment containing the SSU promoter region was ligated with SmaI/EcoRI-digested pUC18 to yield pCGN627.

7.4. Construction of a CaMV Promoter—SPS Transcriptional Fusion

The 35ESS promoter-DNA fragment from cauliflower mosaic virus was fused to the SPS DNA as follows. The plasmid pCGN639 was opened by BamHI and EcoRI and the 3403 bp BamHI-EcoRI SPS cDNA fragment (described in Example 7.1) was cloned into this plasmid. The hybrid gene was removed from this plasmid as a 4.35 kb XbaI-EcoRI fragment and ligated into a binary vector (McBride and Summerfelt, *Plant Mol. Bio.* (1990) 14:269–276) and integrated into a plant genome via *Agrobacterium tumefaciens* mediated transformation. Insertion of the CaMV/SPS construct into the binary vector pCGN1557 (McBride and Summerfelt supra) results in pCGN3815.

7.4.1. Construction of pCGN639 pCGN164 was digested with EcoRV and BamHI to release a EcoRV-BamHI fragment which contained a portion of the 35S promoter (bp 7340–7433). pCG8638 was digested with HindIII and EcoRV to release a HindIII-EcoRV fragment containing a different portion of the 35S promoter (bp 6493–7340). These two fragments were ligated into pCGN986 which had been digested with HindIII and BamHI to remove the HindIII-BamHI fragment containing the 35S-promoter; this ligation produced pCGN639, which contains the backbone and tml-3' region from pCGN986 and the two 35S promoter fragments from pCGN164 and pCGN638.

7.4.2. Construction of pCGN164

The AluI fragment of CaMV (bp 7144–7735) (Gardner et al., *Nucl. Acids Res.* (1981) 9:2871–2888) was obtained by digestion with AluI and cloned into the HincII site of M13mp7 (Vieira and Messing, *Gene* (1982) 19:259–268) to create C614. An EcoRI digest of C614 produced the EcoRI fragment from C614 containing the 35S promoter which was cloned into the EcoRI site of pUC8 (Vieira and Messing, supra) to produce pCGN146. To trim the promoter region, the BglII site (bp 7670) was treated with BglII and Bal31 and subsequently a BglII linker was attached to the Bal31 treated DNA to produce pCGN147. pCGN147 was digested with EcoRI/HphI and the resulting EcoRI-HphI fragment containing the 35S promoter was ligated into EcoRI-SmaI digested M13mp8 (Vieira and Messing, supra) to create pCGN164.

7.4.3. Construction of pCGN638

Digestion of CaMV10 (Gardner, et al., *Nucl. Acids Res.* (1981) 9:2871–2888) with BglII produced a BglII fragment containing a 35S promoter region (bp 6493–7670) which was ligated into the BamHI site of pUC19 (Norrander et al., *Gene* (1983) 26:101–106) to create pCGN638.

7.4.4. Construction of pCGN986 pCGN986 contains a cauliflower mosaic virus 35S (CaMV35) promoter and a T-DNA tml-3' region with multiple restriction sites between them. pCGN986 is derived from another cassette, pCGN206, containing a CaMV35S promoter and a different 3' region, the CaMV region VI 3'-end and pCGN971E, a tml 3' region. pCGN148a containing a promoter region, selectable marker (kanamycin with 2 ATG's) and 3' region, was prepared by digesting pCGN528 with BglII and inserting the BamHI-BglII promoter fragment from pCGN147 (see 7.4.2. above). This fragment was cloned into the BglII site of pCGN528 so that the BglII site was proximal to the kanamycin gene of pCGN528.

The shuttle vector used for this construct pCGN528, is made as follows: pCGN525 was made by digesting a plasmid containing Tn5, which harbors a kanamycin gene (Jorgensen et al., *Mol. Gen. Genet.* (1979) 177:65), with HindIII-BamHI and inserting the HindIII-BamHI fragment containing the kanamycin resistance gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et al., *Cell* (1980) 19:729–739) modified with XhoI linkers inserted into the SmaI site, into the BamHI site of pCGN525. pCGN528 was obtained by deleting the small XhoI and religating.

pCGN149a was made by cloning the BamHI kanamycin gene fragment from pMB9KanXXI into the BamHI site of pCGN148a. pMB9KanXXI is a pUC4K variant (Vieira and Messing, *Gene* (1982) 19:259–268) which has the XhoI site missing but contains a functional kanamycin gene from Tn903 to allow for efficient selection in Agrobacterium.

pCGN149a was digested with HindIII and BamHI and ligated which pUC8 (Vieira and Messing, supra) digested with HindIII and BamHI to produce pCGE169. This removes the Tn903 kanamycin marker. pCGN565 and pCGN169 were both digested with HindIII and PstI and ligated to form pCGN203, a plasmid containing the CaMV 35S promoter and part of the 5'-end of the Tn5 kanamycin gene (up to the PstI site, (Jorgensen et al., *Mol. Gen. Genet.* (1979) 177:65). pCGN565 is a cloning vector based on pUC8-Cm (K. Buckley, Ph.D. Thesis, UC San Diego 1985), but containing the polylinker from pUC18 (Yanisch-Perron et al., *Gene* (1985) 53:103–119). A 3' regulatory region was added to pCGN203 from pCGN204 (an EcoRI fragment of CaMV (bp 408–6105) containing the region VI 3' cloned into pUC18 (Gardner et al., *Nucl. Acids Res.* (1981) 9:2871–2888) by digestion with HindIII and PstI and ligation. The resulting cassette, pCGN206, is the basis for the construction of pCGN986.

The pTiA6 T-DNA tml 3'-sequences were subcloned from the Baml9 T-DNA fragment (Thomashow et al., *Cell* (1980) 19:729–739) as a BamHI-EcoRI fragment (nucleotides 9062 to 12,823, numbering as in Barker et al., *Plant Mol. Biol.* (1983) 2:335–350) and combined with the pACYC184 (Chang and Cohen, *J. Bacteriol.* (1978) 134:1141–1156) origin of replication as an EcoRI-HindII fragment and a gentamycin resistance marker (from plasmid pLB41), (D. Figurski) as a BamHI-HindII fragment to produce pCGN417. The unique SmaI site of pCGN417 (nucleotide 11,207 of the Bam19 fragment) was changed to a SacI site using linkers and the BamHI-SacI fragment was subcloned into pCGN565 to give pCGN971. The BamHI site of pCGN971 was changed to an EcoRI site using linkers to yield pCGN971E. The resulting EcoRI-SacI fragment of pCGN971E, containing the tml 3' regulatory sequence is joined to pCGN206 by digestion with EcoRI and SacI to give pCGN975. The small part of the Tn5 kanamycin resistance gene was deleted from the 3'-end of the CaMV 35S promoter by digestion with SalI and BglII, blunting the ends and ligating with SalI linkers. The final expression cassette, pCGN986, contains the CaMV 35S promoter followed by two SalI sites, an XbaI site, BamHI, SmaI, KpnI sites and the tml 3' region (nucleotides 11207–9023 of the T-DNA).

Figure 10A:
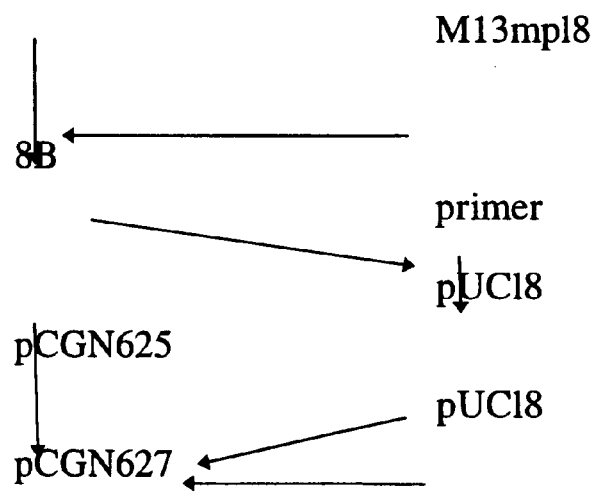
FIGS. 10A–10C show a schematic summary of a construction of plasmids pCGN627, pCGN639 and pCGN986.
Figure 10B:
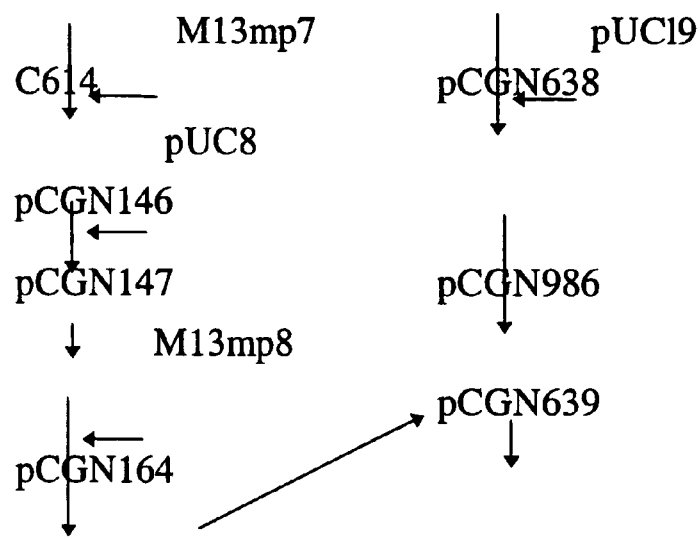
Figure 10C:
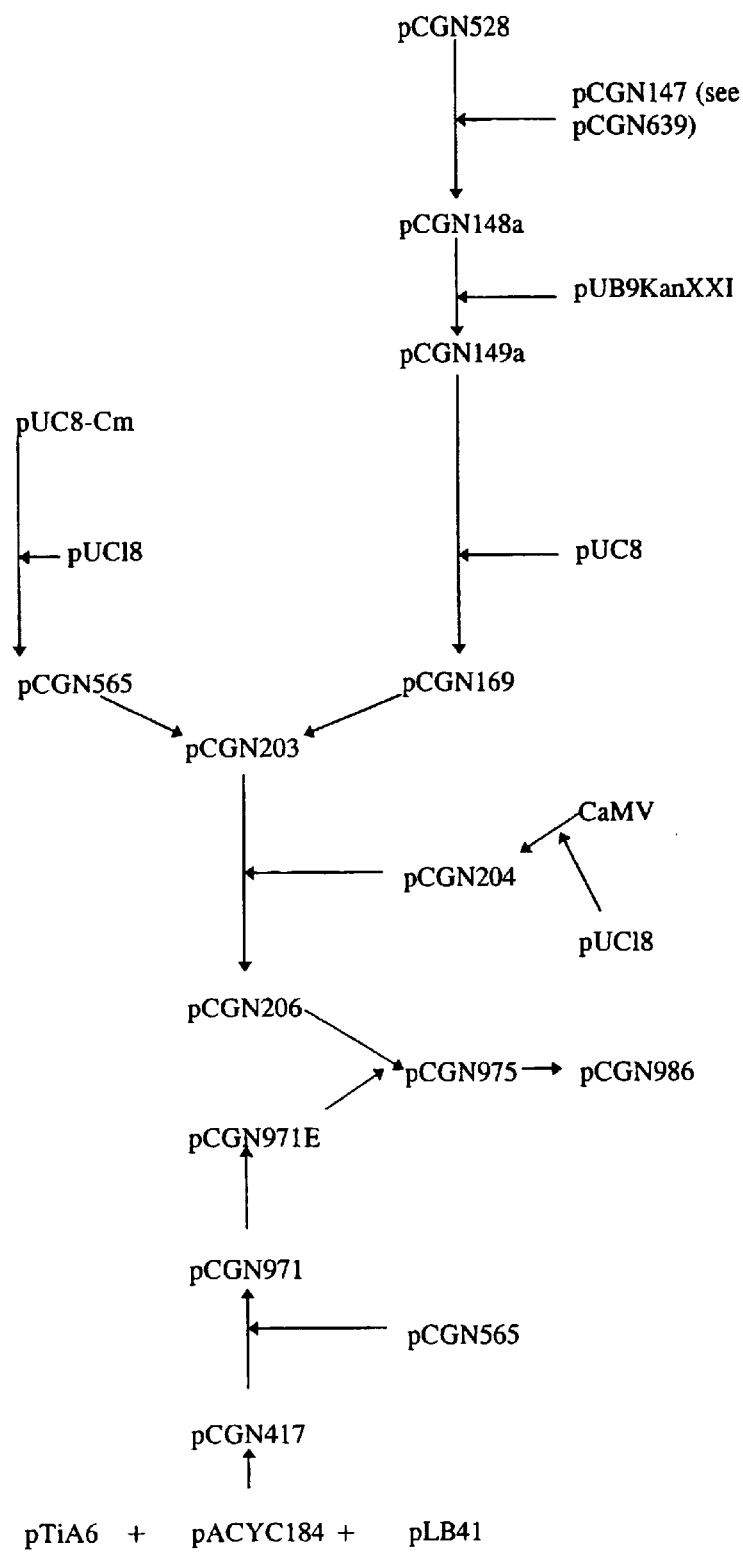

A schematic summary of the construction of the various plasmids is shown in FIGS. 10A through 10C.

Example 8

Transgenic SPS Tomato Plants 8.1 Production of Tissue-Specific SPS "Sense" Transgenic Tomato Plants Tomato plants were transformed with expression cassettes containing SPS encoding sequences (pCGN3812, pCGN3815, pCGN3342, and pCGN3343) via *Agrobacterium tumefaciens* mediated transformation (Fillatti, et al., *Bio/Technology* (1987) 5:726–730) and regenerated. Preparation of pCGN3812, a tobacco SSU/SPS construct, and pCGN3815, a CaMV 35S/SPS construct are described in Examples 7.3 and 7.4, respectively. The fruit-specific E8/SPS constructs pCGN3342 and pCGN3343 were prepared as described for pCGN3812 with the following modifications. Approximately 2.1 kb of the 5' region corresponding to the tomato derived E8 fruit-specific promoter replace the SSU promoter region in pCGN3812. The E8 promoter is described in Deikmann et al. (1988) *EMBOJ*, 2:3315–3320; and Della Penna et al. (1989) *Plant Cell,* 1:53–63. The pCGN3342 and pCGN3343 constructs also contain a SPS cDNA sequence truncated at the ApoI site just 3' of the SPS coding region (at nucleotide 3318), and fused to a 1.2 kb region of the *A. tumefaciens* tml 3' terminator region from pTiA6 (Barker et al., (1983) *Plant Mol. Biol.,* 2:335–350; sequence 11208–10069 of the T-DNA region from *A. tumefaciens* Ti plasmid pTi15955). Constructs pCGN3342 and pCGN3343 represent opposite orientations of the E8-corn SPS-tml insert in the binary vector pCGN1557, which contains the kanamycin nptII marker gene under the control of the CaMV 35S promoter region and the tml 3' terminator region described above for pCGN3318 (McBride and Sumerfelt, *Plant Mol. Biol.* (1990) 14:269–276). Tomato plant lines are designated with a number corresponding to the construct used for transformation. Tomato lines arising from separate transformation events are signified by a hyphen and a number following the construct/plant designation.

8.2 Immunoblot Results

Leaves from transformed tomato plants (pCGN3812 and pCGN3815) and control tomato and corn leaves were tested as described in Example 6.2 for SPS activity using the SPS #30 and SPS #90 peptide polyclonal antisera of Example 6. No cross reactivity between the antisera and the control (endogenous) tomato leaves was seen. This indicates that the corn and tomato SPS are not highly related. As to the transgenic tomato plants, leaf extracts from tomato plants containing the pCGN3815 or pCGN3818 constructs showed signals up to levels several times those observed in the untransformed corn leaf extracts.

8.3 SPS Activity

Leaf extracts also were tested for SPS activity according to the resorcinol protocol described in Example 1.1.a. In comparison to leaf extracts from control plants, leaves from transformed tomato plants containing the SPS gene showed up to 12-fold increases in SPS activity. Higher SPS activity also was observed in some leaf extracts from transgenic tomato plants containing the corn SPS gene as compared to control corn leaf extracts.

8.4 Starch and Sucrose Levels

Leaf tissue was analyzed for starch and sucrose levels according to the method of Haissig, et al., *Physiol. Plan* (1979) 47:151–157. Two controls were used, leaves from an untransformed plant and leaves from a transformant which did not show any corn SPS immunoblot signal. The starch and sucrose levels of these two plants were essentially the same, and had an almost equal percentage of starch (mg/100 mg dry weight) and sucrose (mg/10 mg dry weight). High-expressing plants containing pCGN3812 (pCGN3812-9 and pCGN3812-11) showed both a reduction in leaf starch by 50% and an increase in sucrose levels by a factor of two. Thus, the extra sucrose synthesis provided by the exogenous SPS activity had a profound affect on carbohydrate partitioning. These data indicate that the presence of high levels of corn SPS activity resulting from a sufficient level of transgenic expression of a SPS transgene functional in tomato leaves cause a modification of carbohydrate partitioning in this tissue.

8.5 Oxygen Sensitivity

The interaction between photosynthesis and the synthesis of end products in tomatoes expressing corn SPS was evaluated by gas exchange analysis. Oxygen sensitivity of plants was induced by lowering growth temperature and then $O_2$ sensitivity measured as the rate of photosynthesis in low $O_2$ (Sage and Sharkey (1987) *Plant Physiol.* 84:658–664). Photosynthesis of tomato plants expressing corn SPS became oxygen insensitive at 14.2° C. (measured in 35 Pa $CO_2$), whereas untransformed controls became insensitive at 17.3° C. Change in the growth temperature from 22° C. to 30° C. during the day did not affect this pattern. Furthermore, the transformed plants did not acclimate following growth at high $CO_2$ (Worrell et al. (1991). *The Plant Cell* 3:1121–1131). These data show that the SPS expressing plants have a reduced ceiling imposed on photosynthesis by end product synthesis at lower temperatures. The data also show that the temperature at which photosynthesis becomes oxygen insensitive can be modulated by SPS activity through its effect on chloroplasts, photosynthetic capacity and end product synthesis and sink transport/conversion.

8.6 Temperature Effect on Partitioning

Figure 11:
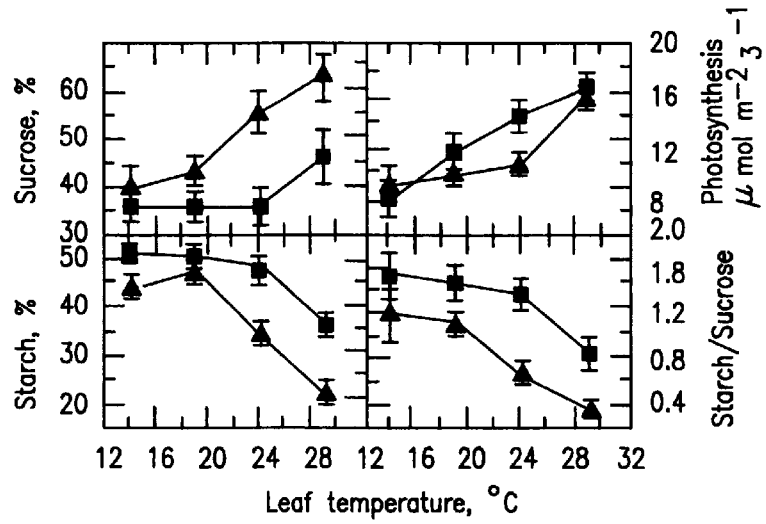
FIG. 11 shows partitioning between starch and sucrose as a function of temperature. The squares are data from control UC82B plants while triangles are data from transgenic tomatoes expressing SPS on a rubisco small subunit promoter (pCGN3812).

The effect of temperature on starch and sucrose partitioning was evaluated in tomato plants transformed with pCGN3812 (see 7.3). The transformed tomato plants were compared to control UC82B plants. The rate of starch plus sucrose synthesis as a function of temperature was assayed by feeding a pulse of $^{14}CO_2$ to leaves at a normal partial pressure then chasing with unlabeled $CO_2$ for a long enough period of time to permit incorporation of the labeled carbon into starch, sucrose, fructose, glucose or another end product but for a short enough period of time so that very little of the carbon was exported from the leaf source tissue. Analysis of end product synthesis showed that sucrose synthesis appeared more sensitive to temperature than did starch synthesis. For example, plants expressing about 5-fold more SPS activity compared to controls did not partition more carbon to sucrose at the lowest temperature. This indicates that the control coefficient for SPS approaches zero as metabolic activity of the plant is reduced with temperature under these conditions. The additional SPS activity also changed the oxygen sensitivity in this same temperature range. The above results show that partitioning between starch and sucrose, end-product synthesis/sink transport and conversion can be modulated as a function of temperature. (See FIG. 11).

8.7 Yield

Manipulation of yield by modification of end-product synthesis is related to growth conditions and reproductive/vegetative sink. The effect of growth conditions on tomato yield was evaluated in homozygous SSU/SPS (Rubisco small subunit promoter-SPS), 35/SPS (CaMV 355 promoter-SPS) and E8/SPS (E8 fruit-specific promoter-SPS) tomato plant lines grown under growth chamber, open-top chamber and field conditions following standard methods in the art.

When compared to untransformed tomato plants, variation in yield increase was observed in the growth chamber, open-top chamber and field trials. Differences observed in fruit yield may be due to earlier flowering and the number of fruits set and filled for plants grown in growth chambers and pots compared to those grown in the field. Also, tomatoes expressing SPS behind the CaMV 35S promoter grew better than tomatoes expressing the gene behind a Rubisco small subunit promoter under growth chamber conditions. These data indicate a promoter effect. Additionally, studies in temperature controlled growth rooms show that there was more yield penalty in the SPS tomatoes at low temperatures than at high temperature. These data are in accordance with the partitioning data showing a reduction in modulation of sucrose levels at low temperature in tomato plants.

8.7.1 Soluble Solids In T2 SSU/SPS Tomato Plants Grown Under Growth Chamber and Greenhouse Conditions Leaf-specific SSU/SPS tomato lines 3812-9 and 3812-11 were evaluated for soluble solid content. Extracts of fruit from these tomato lines and controls were grown and harvested in a Biotron growth chamber or under standard greenhouse conditions and served as the tissue source. T2 plants from the 3812-9 and 3812-11 lines were segregating as the original lines were shown to contain at least two SSU-SPS insertions. For growth chamber conditions, T2 plants were illuminated by metal halide lamps at peak level of 500 $\mu$mol photons/m/s (pot level), at a temperature of 26° C. for the 16 h day and 18° C. at night, and a relative humidity of 60%. Plants were watered daily with half-strength Hoagland's solution (Hoagland and Arnon, *Calif. Argicult. Exp. Sta. Cir.* (1938) 357:1–39). Soluble solids were evaluated as Brix units per unit weight fruit tissue measured for the average of three fruits per plant. Transgenic SSU/SPS plants grown under growth chamber conditions exhibited substantial increases in soluble solids compared to controls. The soluble solids measured in a segregating T2 population of 3812-11 plants grown under greenhouse conditions showed the same effect, but overall increases were reduced compared to SSU/SPS plants in growth chamber tests.

8.7.2 Soluble Solids In T4 SSU/SPS and 35S/SPS Tomato Plants Grown Under Greenhouse Conditions Homozygous SSU/SPS tomato lines were generated from original SSU/SPS 3812-9 transformants in UC82-B tomatoes following standard products. Two homozygous lines designated A and B were grown under greenhouse conditions and fruit evaluated for soluble solid content using Brix analysis measured per unit weight fruit tissue. Soluble solids were measured as an average of three plants per line and three fruit per plant. The average soluble solid content for the SSU/SPS 3812-9 lines was increased significantly compared to the UC82-B controls. The data was shown to be significant at a 0.01% level (99%), according to least significant difference (LSD) statistical analysis.

Homozygous lines of tomato plants transformed with the 35S/SPS construct of pCGN3815 were generated to compare the homozygous leaf-specific SPS construct results to homozygous constitutive expression construct. In one line, designated 3815-13-2, a substantial increase in fruit yield was observed, as measured for both fruit size and fruit number, compared to non-transformed controls and, surprisingly, compared against the SSU/SPS leaf-specific homozygous line controls. The 3815-13-2 plants also produced a second flush of fruit.

8.7.3 Soluble Solids In Field Grown T4 SSU/SPS Tomato Plants

Tomato plants homozygous for the SSU/SPS construct were generated from T4 crosses of original 3812-9 transformants as described in Example 8.1. Tomato lines designated A and B, which arose from separate crossing events, were grown under field conditions following standard field trial protocols. Soluble solids were obtained from fruit extracts of replicate plants as described for growth chamber and greenhouse studies. The soluble solids were evaluated by determining the average refractive index (RI) and specific sugar content per unit weight fruit tissue using high pressure liquid chromatography (HPLC). The RI measurements permitted analysis of overall sugar and acid content and the HPLC analysis for contributions by individual sugars. Both methods of analysis were conducted following standard protocols. The results are reported in Table 11 below.

TABLE 11

Soluble Solids and Sugar Content in Leaf-Specific SSU/SPS Tomato Plants

| Tomato Line | RI | Sucrose | Glucose | Fructose | Total |
|---|---|---|---|---|---|
| Control | 3.9 | 0.08 | 1.33 | 1.62 | 3.03 |
| Control | 4.2 | 0.11 | 1.51 | 1.75 | 3.37 |
| (A) SSU/SPS-A-75-5 | 4.9 | 0.19 | 1.58 | 2.58 | 4.35 |
| (A) SSU/SPS-A-91-4 | 4.9 | 0.19 | 1.61 | 2.55 | 4.35 |
| (B) SSU/SPS-B-87-2 | 4.6 | 0.22 | 1.59 | 2.37 | 4.18 |
| Average increase due to SPS | 0.75 | 0.10 | 0.17 | 0.81 | 1.09 |

Sugar Concentration (%)

The transgenic tomato lines A and B consistently showed higher sugar and acid content compared to the controls. Sucrose, glucose and fructose levels were increased substantially in tomato fruit of the A and B lines, compared to the controls. Surprisingly, the contribution of glucose and fructose to the overall increase in soluble solids was pronounced compared to sucrose, indicating a net partitioning and conversion of photosimilate to the fruit sink tissue.

8.7.4 Soluble Solids In Fruit-Specific E8/SPS Tomato Plants Grown Under Greenhouse Conditions The soluble solids in fruit from tomato plant lines 3342 and 3343 expressing the fruit-specific E8-SPS constructs were evaluated as follows. Tomato plant lines arising from separate transformation events with pCGN3342 and pCGN3343 were grown under standard Greenhouse conditions. Soluble solids from replicate lines and trials were measured using RI, SPS specific activity and HLPC analyses. As a control, untransformed tomato plants and leaf-specific SSU/SPS tomato line were examined in parallel for each trial. Representative data for soluble solid content and distribution are reported in Tables 12–14 below.

TABLE 12

Soluble Solids In Fruit Specific E8/SPS Tomato Plants

| Date of Analysis | Transgenic Tomato Line (RI)[1] | Control Tomato Line (RI)[1] |
|---|---|---|
| | 3343-6 | UC82-B |
| 4/11/95 | 7.2 | 6.0 |
| 4/28/95 | 8.2 | 5.2 |
| 5/30/95 | 10.2 | 7.5 |
| | 3342-11 | UC82-B |
| 3/29/95 | 7.9 | 4.9 |
| 4/4/95 | 7.6 | 6.2 (4/7/95) |
| | 3343-22 | UC82-B |
| 5/10/95 | 7.8 | 6.8 (5/12/95) |
| 5/12/95 | 8.5 | 7.0 |
| 5/16/95 | 7.6 | 6.6 |
| 5/19/95 | 8.2 | |
| | 3343-56 | UC82-B |
| 5/23/95 | 7.6 | 6.1 |
| 5/30/95 | 8.0 | 7.5 |
| 5/31/95 | 9.1 | 6.0 |

[1]Soluble solids measured as refractive index (RI) per unit weight fruit tissue.

TABLE 13

Soluble Solids and Sugar Content In Fruit-Specific E8/SPS Tomato Plants

| Tomato Line | Date | RI | Sucrose | Glucose | Fructose | Total Sugars |
|---|---|---|---|---|---|---|
| Control | 3/29/95 | 4.4 | 0.00 | 2.30 | 1.49 | 3.79 |
| 3342-11 | 3/29/95 | 7.9 | 0.00 | 3.64 | 3.29 | 6.93 |
| 3342-11 | 3/31/95 | 6.1 | 0.00 | 3.02 | 2.48 | 5.50 |
| 3342-11 | 4/4/95 | 7.5 | 0.00 | 3.12 | 3.27 | 6.39 |
| 3342-14 | 3/29/95 | 7.2 | 0.00 | 3.54 | 3.21 | 6.75 |
| 3342-14 | 4/4/95 | 8.4 | 0.00 | 4.13 | 3.72 | 7.85 |
| 3342-23 | 3/29/95 | 8.5 | 0.52 | 3.34 | 3.37 | 7.23 |
| 3343-5 | 4/4/95 | 4.0 | 0.00 | 1.66 | 1.27 | 2.93 |
| 3812-6 | 4/4/95 | 8.5 | 0.00 | 3.95 | 3.57 | 7.52 |

Sugar Concentration (%)

TABLE 14

Soluble Solids, Sugar Content and Acid Content In Fruit-Specific E8/SPS Tomato Plants

| Tomato Line | Date | RI | Sugar Concentration (%) | | | | Total Sugars | Titratable Acidity |
|---|---|---|---|---|---|---|---|---|
| | | | Sucrose | Glucose | Fructose | Glucose/Fructose | | |
| 7060 | 5/19/95 | 6.6 | N.D. | 3.10 | 2.78 | 1.12 | 5.88 | 0.384 |
| 3343-22 | 5/19/95 | 8.2 | N.D. | 4.40 | 3.75 | 1.16 | 8.18 | 0.608 |
| 3342-16 | 5/19/95 | 8.2 | N.D. | 4.23 | 3.71 | 1.14 | 7.95 | 0.555 |
| FL7060 | 5/31/95 | 6.2 | N.D. | 3.01 | 2.36 | 1.28 | 5.37 | 0.448 |
| 3343-56 | 5/31/95 | 8.1 | N.D. | 4.64 | 4.08 | 1.14 | 8.72 | N.D. |
| 3812-29 | 5/31/95 | 9.5 | N.D. | 5.13 | 4.21 | 1.22 | 9.33 | N.D. |
| 3343-6 | 5/30/95 | 10.4 | 0.36 | 4.91 | 4.69 | 1.05 | 9.97 | .0597 |
| 3343-6 | 5/2/95 | 8.2 | N.D. | 3.95 | 3.68 | 1.07 | 7.63 | .0640 |
| FL7060 | 5/2/95 | 4.9 | N.D. | 2.33 | 1.79 | 1.30 | 4.11 | 0.432 |
| FL7060 | 5/12/95 | 6.8 | N.D. | 3.46 | 2.84 | 1.21 | 6.29 | 0.533 |
| 3343-22 | 5/12/95 | 8.5 | N.D. | 4.24 | 3.57 | 1.19 | 7.81 | N.D. |

Tomato plant lines expressing the fruit-specific E8/SPS constructs consistently showed an increase in soluble solids reflected by overall sugar content, acid content and distribution. To assess the correlation between SPS activity and altered soluble solid content, SPS activity was measured in fruit from control tomato plants and compared to that in fruit from E8/SPS tomato lines 3343-6 and 3342-11. Control fruit from tomato line FL7060 was assayed with a SPS activity rate of 17.8 μmols sucrose/gram fresh weight/hour. Activity was much higher in the transgenic lines, with the 3343-6 event having a rate of 67.5 μmols sucrose/grown fresh weight/hour and the 3342-11 event measured at 36.6 μmols sucrose/gram fresh weight/hour. These results show that the increase of fruit-specific activity of the SPS correlates to the increase in sugar content of fruit.

Example 9

Transgenic SPS Potato Plants 9.1 Production of SPS Potato Plants

Potato plants were transformed with expression cassettes containing SPS coding sequences (pCGN3812) via *Agrobacterium tumefaciens* mediated transformation (Fillatti et al., supra) and regenerated. Preparation of pCGN3812, a tobacco SSU/SPS construct, is described in Example 4.3.

9.2 Oxygen Sensitivity

Figure 12:
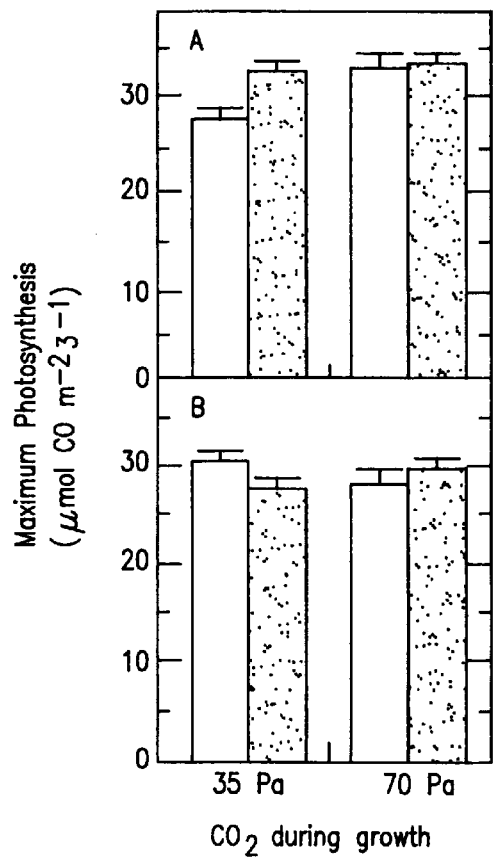
FIGS. 12A–12B show maximum rates of photosynthesis for regenerated control (solid bars) and pCGN3812-24 transgenic (open bars) potatoes at three weeks after (panel A) and seven weeks after (panel B) planting.

Potato is adapted to cool weather and has a large vegetative sink, whereas the genetically similar tomato has a large reproductive sink. To evaluate whether potato has a relatively higher capacity for starch plus sucrose synthesis, allowing it to avoid oxygen insensitivity in the range of 12° C. to 20° C., oxygen sensitivity was examined in potatoes expressing the corn SPS gene. Potatoes expressing the corn SPS exhibited a higher capacity for photosynthesis in elevated $CO_2$ when the plants were three weeks old compared to controls. When the potato corn SPS expressing plants were six to seven weeks old with developing tubers, they showed the acclimation to elevated $CO_2$ found in many plants and the controls (FIG. 12). These data show that responsiveness of plant growth to elevated $C0_2$ in plants having diverse physiological systems can be modulated by manipulating sucrose synthesis through an SPS which functions in plants.

9.3 Tuber Yield

Figure 13A:
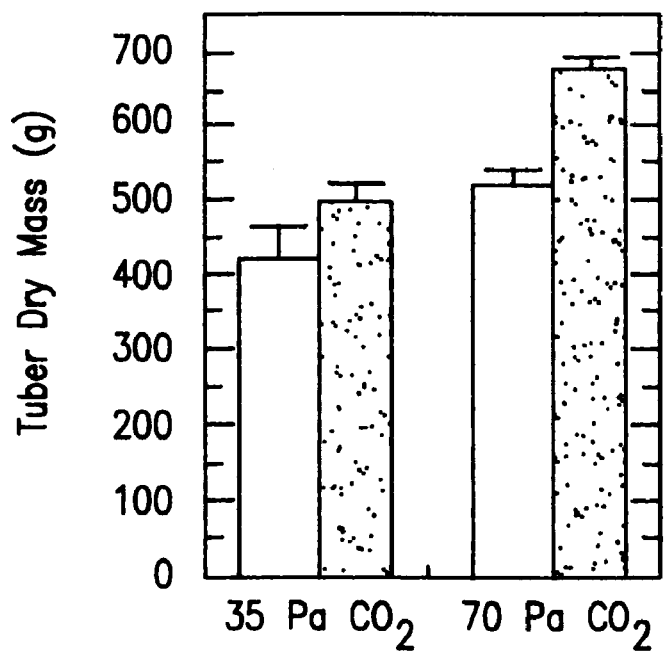
FIGS. 13A–13B show tuber dry mass for regenerated control (solid bars) and pCGN3812-24 transgenic (open bars) potatoes add 35 and 70 Pa carbon dioxide in highlight growth chambers (FIG. 13A) and open top chambers in the field (FIG. 13B).
Figure 13B:
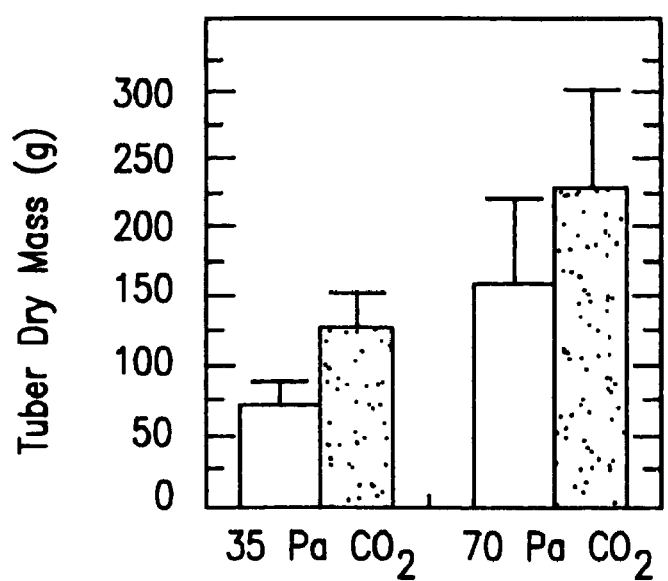

Transformed potatoes expressing corn SPS exhibited greater tuber yield when grown in both large chambers and in open top chambers out-of-doors (FIG. 13). Because yield in potato is tuber mass and not fruit, the effect in potato appear different from the effect seen in tomato. Collectively, the tomato and potato yield data indicate that modification of SPS activity through expression of an exogenous transgene encoding SPS directly effects net sucrose synthesis and mass action in a simialr manner in diverse plant systems, even though sucrose metabolism and its systemic effects may differ, which can be used to manipulate yield.

The above results demonstrate that transgenic plants can be constructed which have altered carbon partitioning through expression of a gene required for sucrose synthesis. Plants transformed with a DNA expression construct capable of controlling the expression of an SPS gene exhibited modification of starch and sucrose levels, $CO_2$ and/or $O_2$ sensitivity, temperature dependent growth responsiveness, and overall modification of carbon partitioning between source tissue such as leaf and sink tissue such as fruit or root. The data also show that the plant growth and yield were affected by altered carbon partitioning, as illustrated in two different plants of the nightshade family Solanaceae, potato and tomato. The data also show that control of carbohydrate partitioning through modification of end-product synthesis, for example, sucrose synthesis and conversion to other sugars in sink tissue, such as glucose and fructose provide means for altering plant growth and yield of specific plant tissues, plant parts and/or whole plant systems. In particular, increased SPS activity and tissue-specific SPS activity was demonstrated to produce a net increase in overall soluble solids in sink tissue such as fruit. Increases in the sugars sucrose, glucose and fructose represented soluble sugars analyzed in the soluble solids, with contributions by glucose and fructose being higher than sucrose. The SPS activity and sugar content data indicate that the endogenous acid invertase found in ripening tomato fruit contributed to the observed increases in glucose and fructose.

Acid levels in the fruit-specific E8/SPS constructs also were observed, correlating acid content to an increase in sugar content. These data collectively show that SPS can be used to alter the overall content and ratio of soluble solids in a plant sink tissue, resulting in a demonstrable phenotype in plants, such as fruit having modified sweetness. Also, tomatoes expressing SPS behind the CaMV 35S promoter grew better than tomatoes expressing the gene behind a Rubisco small subunit promoter under growth chamber conditions. These data indicate a promoter effect which can be manipulated to control SPS activity in particular plant cells, plant parts and throughout the plant. In general, the results show that plant growth and yield can be enhanced through transgenic expression of SPS, even though its effect on photosynthesis may be small.

All publications and patent applications mentioned in the specification are indicative of the level of skill of those skilled in the art to which this invention pertains. All referenced publications and patent applications are herein incorporated by reference to the same extent as if each individual publication or patent application was specifically and individually indicated to be incorporated by reference.

The invention now being fully described, it would be apparent to one of ordinary skill in the art that many changes and modifications can be made thereto without departing from the spirit or scope of the appended claims.

What is claimed is:

1. A method of increasing the level of sucrose phosphate synthase activity in a plant cell comprising:
   transforming a plant cell with a transgene comprising as operably linked components in the 5' to 3' direction of transcription, a transcription initiation region and a DNA encoding a sucrose phosphate synthase, wherein said DNA encoding a sucrose phosphate synthase is in the sense orientation, whereby said DNA encoding a sucrose phosphate synthase is expressed at a level which increases the level of sucrose phosphate synthase activity in said plant cell as compared to control plant cells.

2. The method of claim 1, wherein said plant cell is selected from the group consisting of a leaf cell, a fruit cell, and a root cell.

3. The method of claim 1, wherein said DNA encoding a sucrose phosphate synthase comprises a DNA sequence having at least about 10 nucleotides up to the full length of nucleotides represented by SEQ ID NO: 6.

4. The method of claim 3, wherein said DNA sequence encodes an amino acid sequence represented by a SEQ ID NO selected from the group consisting of SEQ ID NO: 1, SEQ ID NO:2, SEQ ID NO:3, SEQ ID NO:4, and SEQ ID NO:5.

5. The method of claim 3, wherein said DNA is cDNA.

6. The method of claim 1, wherein said transgene further comprises a translation initiation region operably linked 3' to said transcription initiation region and 5' to said DNA encoding a sucrose phosphate synthase and a transcription termination region 3' to said DNA encoding a sucrose phosphate synthase, wherein said translation initiation region and said transcription termination region are functional in said plant cell.

7. The method of claim 6, wherein said transcription termination region is a sucrose phosphate synthase gene transcription termination region.

8. The method of claim 1, wherein said transcription initiation region is tissue specific.

9. The method of claim 8, wherein said transcription initiation region is specific for a tissue selected from the group consisting of leaf, fruit, and root.

10. The method of claim 1, wherein said sucrose phosphate synthase activity affects sucrose synthesis.

11. The method of claim 10, wherein said sucrose synthesis is increased in said plant cell as compared to control plant cells.

12. The method of claim 1, wherein increasing the level of sucrose phosphate synthesis activity increases the level of soluble solids in said plant cell as compared to control plant cells.

13. The method of claim 12, wherein said soluble solids are selected from the group consisting of sucrose, glucose and fructose.

14. The method of claim 1, wherein increasing the level of sucrose phosphate synthase activity modifies the carbon partitioning in said plant cell as compared to control plant cells.

15. The method of claim 14, wherein said carbon partitioning in said plant cell is the ratio of starch to sucrose in said cell.

16. A method of modifying the level of sucrose phosphate synthase activity in a plant cell comprising:
   transforming a plant cell with a transgene comprising as operably linked components in the 5' to 3' direction of transcription, a transcription initiation region and a DNA comprising the nucleic acid sequence of SEQ ID NO:6 encoding a sucrose phosphate synthase, whereby said DNA is expressed at a level which modifies the level of sucrose phosphate synthase activity in said cell as compared to control plant cells.

17. A method of decreasing the level of sucrose phosphate synthase activity in a plant cell comprising:
   transforming a plant cell with a transgene comprising as operably linked components in the 5' to 3' direction of transcription, a transcription initiation region and a DNA encoding a sucrose phosphate synthase, wherein said DNA encoding a sucrose phosphate synthase is in the antisense orientation, whereby said DNA encoding a sucrose phosphate synthase is expressed at a level which decreases the level of sucrose phosphate synthase activity in said plant cell as compared to control plant cells.

18. A plant cell which comprises and expresses a transgene comprising as operably linked components in the 5' to 3' direction of transcription, a transcription initiation region and a DNA encoding a sucrose phosphate synthase functional in said plant cell.

19. The plant cell of claim 18, wherein said DNA encoding a sucrose phosphate synthase is cDNA.

20. The plant cell of claim 18, wherein said DNA encoding a sucrose phosphate synthase is in the sense orientation.

21. The plant cell of claim 18, wherein said plant cell is selected from the group consisting of a leaf cell, a fruit cell, and a root cell.

22. The plant cell of claim 20, wherein said transcription initiation region is tissue specific.

23. The plant cell of claim 22, wherein said tissue is selected from the group consisting of a leaf, a fruit, and a root.

24. The plant cell of claim 18, wherein said plant cell has a modified level of sucrose phosphate synthase activity as compared to control plant cells.

25. The plant cell of claim 24, wherein said modified level of sucrose phosphate synthase activity is an increased level of sucrose phosphate synthase activity as compared to control plant cells.

26. A plant cell which contains and expresses a transgene comprising as operably linked components in the 5' to 3' direction of transcription, a transcription initiation region and a DNA comprising the nucleic acid sequence of SEQ ID NO:6 encoding a sucrose phosphate synthase functional in said plant cell.

27. A plant comprising a plant cell according to claim 18, wherein said DNA encoding a sucrose phosphate synthase is in the sense orientation.

28. A transgenic plant which comprises and expresses one or more copies of a transgene comprising as operably linked components in the 5' to 3' direction of transcription, a transcription initiation region and a DNA encoding a sucrose phosphate synthase functional in said transgenic plant, wherein said transgenic plant has increased sucrose phosphate synthase activity as compared to a control plant.

29. The transgenic plant of claim 28, wherein said transgenic plant is a member of the family Solanaceae.

30. The transgenic plant of claim 29, wherein said member is a tomato or a potato.

31. A plant comprising a plant cell according to claim 26.

32. A plant comprising a plant cell according to claim 18, wherein said DNA encoding a sucrose phosphate synthase is in the antisense orientation.

33. A transgenic plant which comprises and expresses one or more copies of a transgene comprising as operably linked components in the 5' to 3' direction of transcription, a transcription initiation region and a DNA encoding a sucrose phosphate synthase functional in said transgenic plant, wherein said DNA encoding a sucrose phosphate synthase is in the antisense orientation, and wherein said transgenic plant has decreased sucrose phosphate synthase activity as compared to a control plant.

34. A method of increasing the yield of a plant sink tissue, said method comprising:
transforming a plant which comprises one or more copies of a transgene comprising as operably linked components in the 5' to 3' direction of transcription, a transcription initiation region functional in said plant and a DNA encoding a sucrose phosphate synthase functional in said plant, wherein said DNA encoding a sucrose phosphate synthase is in the sense orientation, whereby said transgene is expressed at a level which increases the sucrose phosphate synthase activity in said plant, whereby said yield of said plant sink tissue is increased.

35. The method of claim 34, wherein said plant is a member of the family Solanaceae.

36. The method of claim 35, wherein said member is a tomato or a potato.

37. A method of increasing the yield of a plant sink tissue, said method comprising:
transforming a plant with one or more copies of a transgene comprising DNA encoding a sucrose phosphate synthase functional in said plant, whereby the sucrose phosphate synthase activity in said plant is increased to a level sufficient to increase the flow of sucrose to said plant sink tissue as compared to the flow of sucrose to a control plant sink tissue, whereby the yield of said plant sink tissue is increased as compared to a control plant sink tissue.

38. The method of claim 37, wherein expression of said transgene is tissue specific.

39. The method of claim 38, wherein said tissue specific expression is in a tissue selected from the group consisting of leaf, fruit and root.

40. The method of claim 37, wherein said plant sink tissue is selected from the group consisting of leaf tissue, fruit tissue, and root tissue.

41. The method of claim 37, wherein said plant is a member of the family Solanaceae.

42. The method of claim 41, wherein said member is a tomato or a potato.

43. A method of increasing the yield of a plant sink tissue, said method comprising:
transforming a plant with one or more copies of a transgene comprising a DNA comprising the nucleic acid sequence of SEQ ID NO:6 encoding a sucrose phosphate synthase, whereby the sucrose phosphate synthase activity in said plant is increased to a level sufficient to increase the flow of sucrose to said plant sink tissue as compared to the flow of sucrose to a control plant sink tissue, whereby the yield of said plant sink tissue is increased as compared to a control plant sink tissue.

44. A method for modifying the soluble solids in a plant sink tissue, said method comprising:
transforming a plant with a transgene comprising as operably linked components in the 5' to 3' direction of transcription, a transcription initiation region and a DNA encoding a sucrose phosphate synthase functional in said plant, wherein said DNA encoding a sucrose phosphate synthase is in the sense orientation, whereby said DNA encoding a sucrose phosphate synthase is expressed at a level which increases the amount of soluble solids per unit weight of said sink tissue compared to the amount of soluble solids per unit weight in a control plant sink tissue.

45. The method of claim 44, wherein said weight is fresh weight.

46. The method of claim 44, wherein said sink tissue is fruit tissue.

47. The method of claim 44, wherein the amount of glucose and fructose in said sink tissue is increased compared to the amount of glucose and fructose measured in a control plant sink tissue.

48. The method of claim 44, wherein said plant is a member of the family Solanaceae.

49. The method of claim 48, wherein said member is a tomato or a potato.

50. A method of increasing the yield of a plant fruit, said method comprising:
transforming a plant with one or more copies of a transgene comprising DNA encoding a sucrose phosphate synthase, whereby the sucrose phosphate synthase activity in said plant is increased to a level sufficient to increase the flow of sucrose said fruit as compared to the flow of sucrose to a control fruit, whereby the yield of said fruit is increased as compared to a control fruit.

51. The method of claim 50, wherein the amount of glucose and fructose in said fruit is increased compared to the amount of glucose and fructose measured in a control fruit.

52. The method of claim 50, wherein said plant is a member of the family Solanaceae.

53. The method of claim 52, wherein said member is a tomato or a potato.

54. A method for modifying total sugars in a plant sink tissue, said method comprising:

transforming a plant with a transgene comprising as operably linked components in the 5' to 3' direction of transcription, a transcription initiation region and a DNA encoding a sucrose phosphate synthase, wherein said DNA encoding a sucrose phosphate synthase is in the sense orientation, whereby said DNA encoding a sucrose phosphate synthase is expressed at a level which increases the total sugars per unit weight of said plant sink tissue as compared to the total sugars per unit weight in a control plant sink tissue.

55. The method of claim 54, wherein said sink tissue is fruit tissue.

56. The method of claim 54, wherein said plant is a member of the family Solanaceae.

57. The method of claim 54, wherein said member is a tomato.

* * * * *

```
                          SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Thr Trp Ile Lys
     1

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Tyr Val Val Glu Leu Ala Arg
     1               5

(2) INFORMATION FOR SEQ ID NO:3:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:3:

Ser Met Pro Pro Ile Trp Ala Glu Val Met Arg
     1               5                  10

(2) INFORMATION FOR SEQ ID NO:4:

(i) SEQUENCE CHARACTERISTICS:
         (A) LENGTH: 14 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:4:

Leu Arg Pro Asp Gln Asp Tyr Leu Met His Ile Ser His Arg
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Trp Ser His Asp Gly Ala Arg
    1             5

(2) INFORMATION FOR SEQ ID NO:6:

(i) SEQUENCE CHARACTERISTICS:
        (A) LENGTH: 3509 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 112..3315

(xi) SEQUENCE DESCRIPTION: SEQ ID NO:6:

```
GAATTCCGGC GTGGGCGCTG GGCTAGTGCT CCCGCAGCGA GCGATCTGAG AGAACGGTAG         60

AGTTCCGGCC GGGCGCGCGG GAGAGGAGGA GGGTCGGGCG GGAGGATCC G ATG GCC         117
                                                         Met Ala
                                                           1

GGG AAC GAG TGG ATC AAT GGG TAC CTG GAG GCG ATC CTC GAC AGC CAC         165
Gly Asn Glu Trp Ile Asn Gly Tyr Leu Glu Ala Ile Leu Asp Ser His
      5                  10                  15

ACC TCG TCG CGG GGT GCC GGC GGC GGC GGC GGG GGG GAC CCC AGG             213
Thr Ser Ser Arg Gly Ala Gly Gly Gly Gly Gly Gly Asp Pro Arg
 20                  25                  30

TCG CCG ACG AAG GCG GCG AGC CCC CGC GGC GCG CAC ATG AAC TTC AAC         261
Ser Pro Thr Lys Ala Ala Ser Pro Arg Gly Ala His Met Asn Phe Asn
 35                  40                  45                  50

CCC TCG CAC TAC TTC GTC GAG GAG GTG GTC AAG GGC GTC GAC GAG AGC         309
Pro Ser His Tyr Phe Val Glu Glu Val Val Lys Gly Val Asp Glu Ser
                 55                  60                  65

GAC CTC CAC CGG ACG TGG ATC AAG GTC GTC GCC ACC CGC AAC GCC CGC         357
Asp Leu His Arg Thr Trp Ile Lys Val Val Ala Thr Arg Asn Ala Arg
             70                  75                  80

GAG CGC AGC ACC AGG CTC GAG AAC ATG TGC TGG CGG ATC TGG CAC CTC         405
Glu Arg Ser Thr Arg Leu Glu Asn Met Cys Trp Arg Ile Trp His Leu
         85                  90                  95

GCG CGC AAG AAG AAG CAG CTG GAG CTG GAG GGC ATC CAG AGA ATC TCG         453
Ala Arg Lys Lys Lys Gln Leu Glu Leu Glu Gly Ile Gln Arg Ile Ser
100                 105                 110

GCA AGA AGG AAG GAA CAG GAG CAG GTG CGT CGT GAG GCG ACG GAG GAC         501
Ala Arg Arg Lys Glu Gln Glu Gln Val Arg Arg Glu Ala Thr Glu Asp
115                 120                 125                 130

CTG GCC GAG GAT CTG TCA GAA GGC GAG AAG GGA GAC ACC ATC GGC GAG         549
Leu Ala Glu Asp Leu Ser Glu Gly Glu Lys Gly Asp Thr Ile Gly Glu
                135                 140                 145

CTT GCG CCG GTT GAG ACG ACC AAG AAG AAG TTC CAG AGG AAC TTC TCT         597
Leu Ala Pro Val Glu Thr Thr Lys Lys Lys Phe Gln Arg Asn Phe Ser
            150                 155                 160
```

-continued

```
GAC CTT ACC GTC TGG TCT GAC GAC AAT AAG GAG AAG AAG CTT TAC ATT         645
Asp Leu Thr Val Trp Ser Asp Asp Asn Lys Glu Lys Lys Leu Tyr Ile
            165                 170                 175

GTG CTC ATC AGC GTG CAT GGT CTT GTT CGT GGA GAA AAC ATG GAA CTA         693
Val Leu Ile Ser Val His Gly Leu Val Arg Gly Glu Asn Met Glu Leu
        180                 185                 190

GGT CGT GAT TCT GAT ACA GGT GGC CAG GTG AAA TAT GTG GTC GAA CTT         741
Gly Arg Asp Ser Asp Thr Gly Gly Gln Val Lys Tyr Val Val Glu Leu
195                 200                 205                 210

GCA AGA GCG ATG TCA ATG ATG CCT GGA GTG TAC AGG GTG GAC CTC TTC         789
Ala Arg Ala Met Ser Met Met Pro Gly Val Tyr Arg Val Asp Leu Phe
                215                 220                 225

ACT CGT CAA GTG TCA TCT CCT GAC GTG GAC TGG AGC TAC GGT GAG CCA         837
Thr Arg Gln Val Ser Ser Pro Asp Val Asp Trp Ser Tyr Gly Glu Pro
            230                 235                 240

ACC GAG ATG TTA TGC GCC GGT TCC AAT GAT GGA GAG GGG ATG GGT GAG         885
Thr Glu Met Leu Cys Ala Gly Ser Asn Asp Gly Glu Gly Met Gly Glu
        245                 250                 255

AGT GGC GGA GCC TAC ATT GTG CGC ATA CCG TGT GGG CCG CGG GAT AAA         933
Ser Gly Gly Ala Tyr Ile Val Arg Ile Pro Cys Gly Pro Arg Asp Lys
260                 265                 270

TAC CTC AAG AAG GAA GCG TTG TGG CCT TAC CTC CAA GAG TTT GTC GAT         981
Tyr Leu Lys Lys Glu Ala Leu Trp Pro Tyr Leu Gln Glu Phe Val Asp
275                 280                 285                 290

GGA GCC CTT GCG CAT ATC CTG AAC ATG TCC AAG GCT CTG GGA GAG CAG        1029
Gly Ala Leu Ala His Ile Leu Asn Met Ser Lys Ala Leu Gly Glu Gln
                295                 300                 305

GTT GGA AAT GGG AGG CCA GTA CTG CCT TAC GTG ATA CAT GGG CAC TAT        1077
Val Gly Asn Gly Arg Pro Val Leu Pro Tyr Val Ile His Gly His Tyr
            310                 315                 320

GCC GAT GCT GGA GAT GTT GCT GCT CTC CTT TCT GGT GCG CTG AAT GTG        1125
Ala Asp Ala Gly Asp Val Ala Ala Leu Leu Ser Gly Ala Leu Asn Val
        325                 330                 335

CCA ATG GTG CTC ACT GGC CAC TCA CTT GGG AGG AAC AAG CTG GAA CAA        1173
Pro Met Val Leu Thr Gly His Ser Leu Gly Arg Asn Lys Leu Glu Gln
340                 345                 350

CTG CTG AAG CAA GGG CGC ATG TCC AAG GAG GAG ATC GAT TCG ACA TAC        1221
Leu Leu Lys Gln Gly Arg Met Ser Lys Glu Glu Ile Asp Ser Thr Tyr
355                 360                 365                 370

AAG ATC ATG AGG CGT ATC GAG GGT GAG GAG CTG GCC CTG GAT GCG TCA        1269
Lys Ile Met Arg Arg Ile Glu Gly Glu Glu Leu Ala Leu Asp Ala Ser
                375                 380                 385

GAG CTT GTA ATC ACG AGC ACA AGG CAG GAG ATT GAT GAG CAG TGG GGA        1317
Glu Leu Val Ile Thr Ser Thr Arg Gln Glu Ile Asp Glu Gln Trp Gly
            390                 395                 400

TTG TAC GAT GGA TTT GAT GTC AAG CTT GAG AAA GTG CTG AGG GCA CGG        1365
Leu Tyr Asp Gly Phe Asp Val Lys Leu Glu Lys Val Leu Arg Ala Arg
        405                 410                 415

GCG AGG CGC GGG GTT AGC TGC CAT GGT CGT TAC ATG CCT AGG ATG GTG        1413
Ala Arg Arg Gly Val Ser Cys His Gly Arg Tyr Met Pro Arg Met Val
420                 425                 430

GTG ATT CCT CCG GGA ATG GAT TTC AGC AAT GTT GTA GTT CAT GAA GAC        1461
Val Ile Pro Pro Gly Met Asp Phe Ser Asn Val Val Val His Glu Asp
435                 440                 445                 450

ATT GAT GGG GAT GGT GAC GTC AAA GAT GAT ATC GTT GGT TTG GAG GGT        1509
Ile Asp Gly Asp Gly Asp Val Lys Asp Asp Ile Val Gly Leu Glu Gly
                455                 460                 465

GCC TCA CCC AAG TCA ATG CCC CCA ATT TGG GCC GAA GTG ATG CGG TTC        1557
Ala Ser Pro Lys Ser Met Pro Pro Ile Trp Ala Glu Val Met Arg Phe
            470                 475                 480
```

```
CTG ACC AAC CCT CAC AAG CCG ATG ATC CTG GCG TTA TCA AGA CCA GAC    1605
Leu Thr Asn Pro His Lys Pro Met Ile Leu Ala Leu Ser Arg Pro Asp
            485                 490                 495

CCG AAG AAG AAC ATC ACT ACC CTC GTC AAA GCC TTT GGA GAG TGT CGT    1653
Pro Lys Lys Asn Ile Thr Thr Leu Val Lys Ala Phe Gly Glu Cys Arg
500                 505                 510

CCA CTC AGG GAA CTT GCA AAC CTT ACT CTG ATC ATG GGT AAC AGA GAT    1701
Pro Leu Arg Glu Leu Ala Asn Leu Thr Leu Ile Met Gly Asn Arg Asp
515                 520                 525                 530

GAC ATC GAC GAC ATG TCT GCT GGC AAT GCC AGT GTC CTC ACC ACA GTT    1749
Asp Ile Asp Asp Met Ser Ala Gly Asn Ala Ser Val Leu Thr Thr Val
                535                 540                 545

CTG AAG CTG ATT GAC AAG TAT GAT CTG TAC GGA AGC GTG GCG TTC CCT    1797
Leu Lys Leu Ile Asp Lys Tyr Asp Leu Tyr Gly Ser Val Ala Phe Pro
            550                 555                 560

AAG CAT CAC AAT CAG GCT GAC GTC CCG GAG ATC TAT CGC CTC GCG GCC    1845
Lys His His Asn Gln Ala Asp Val Pro Glu Ile Tyr Arg Leu Ala Ala
            565                 570                 575

AAA ATG AAG GGC GTC TTC ATC AAC CCT GCT CTC GTT GAG CCG TTT GGT    1893
Lys Met Lys Gly Val Phe Ile Asn Pro Ala Leu Val Glu Pro Phe Gly
580                 585                 590

CTC ACC CTG ATC GAG GCT GCG GCA CAC GGA CTC CCG ATA GTC GCT ACC    1941
Leu Thr Leu Ile Glu Ala Ala Ala His Gly Leu Pro Ile Val Ala Thr
595                 600                 605                 610

AAG AAT GGT GGT CCG GTC GAC ATT ACA AAT GCA TTA AAC AAC GGA CTG    1989
Lys Asn Gly Gly Pro Val Asp Ile Thr Asn Ala Leu Asn Asn Gly Leu
                615                 620                 625

CTC GTT GAC CCA CAC GAC CAG AAC GCC ATC GCT GAT GCA CTG CTG AAG    2037
Leu Val Asp Pro His Asp Gln Asn Ala Ile Ala Asp Ala Leu Leu Lys
            630                 635                 640

CTT GTG GCA GAC AAG AAC CTG TGG CAG GAA TGC CGG AGA AAC GGG CTG    2085
Leu Val Ala Asp Lys Asn Leu Trp Gln Glu Cys Arg Arg Asn Gly Leu
            645                 650                 655

CGC AAC ATC CAC CTC TAC TCA TGG CCG GAG CAC TGC CGC ACT TAC CTC    2133
Arg Asn Ile His Leu Tyr Ser Trp Pro Glu His Cys Arg Thr Tyr Leu
660                 665                 670

ACC AGG GTG GCC GGG TGC CGG TTA AGG AAC CCG AGG TGG CTG AAG GAC    2181
Thr Arg Val Ala Gly Cys Arg Leu Arg Asn Pro Arg Trp Leu Lys Asp
675                 680                 685                 690

ACA CCA GCA GAT GCC GGA GCC GAT GAG GAG GAG TTC CTG GAG GAT TCC    2229
Thr Pro Ala Asp Ala Gly Ala Asp Glu Glu Glu Phe Leu Glu Asp Ser
                695                 700                 705

ATG GAC GCT CAG GAC CTG TCA CTC CGT CTG TCC ATC GAC GGT GAG AAG    2277
Met Asp Ala Gln Asp Leu Ser Leu Arg Leu Ser Ile Asp Gly Glu Lys
            710                 715                 720

AGC TCG CTG AAC ACT AAC GAT CCA CTG TGG TTC GAC CCC CAG GAT CAA    2325
Ser Ser Leu Asn Thr Asn Asp Pro Leu Trp Phe Asp Pro Gln Asp Gln
            725                 730                 735

GTG CAG AAG ATC ATG AAC AAC ATC AAG CAG TCG TCA GCG CTT CCT CCG    2373
Val Gln Lys Ile Met Asn Asn Ile Lys Gln Ser Ser Ala Leu Pro Pro
            740                 745                 750

TCC ATG TCC TCA GTC GCA GCC GAG GGC ACA GGC AGC ACC ATG AAC AAA    2421
Ser Met Ser Ser Val Ala Ala Glu Gly Thr Gly Ser Thr Met Asn Lys
755                 760                 765                 770

TAC CCA CTC CTG CGC CGG CGC CGG CGC TTG TTC GTC ATA GCT GTG GAC    2469
Tyr Pro Leu Leu Arg Arg Arg Arg Arg Leu Phe Val Ile Ala Val Asp
            775                 780                 785

TGC TAC CAG GAC GAT GGC CGT GCT AGC AAG AAG ATG CTG CAG GTG ATC    2517
Cys Tyr Gln Asp Asp Gly Arg Ala Ser Lys Lys Met Leu Gln Val Ile
            790                 795                 800
```

```
CAG GAA GTT TTC AGA GCA GTC CGA TCG GAC TCC CAG ATG TTC AAG ATC    2565
Gln Glu Val Phe Arg Ala Val Arg Ser Asp Ser Gln Met Phe Lys Ile
            805                 810                 815

TCA GGG TTC ACG CTG TCG ACT GCC ATG CCG TTG TCC GAG ACA CTC CAG    2613
Ser Gly Phe Thr Leu Ser Thr Ala Met Pro Leu Ser Glu Thr Leu Gln
820                 825                 830

CTT CTG CAG CTC GGC AAG ATC CCA GCG ACC GAC TTC GAC GCC CTC ATC    2661
Leu Leu Gln Leu Gly Lys Ile Pro Ala Thr Asp Phe Asp Ala Leu Ile
835                 840                 845                 850

TGT GGC AGC GGC AGC GAG GTG TAC TAT CCT GGC ACG GCG AAC TGC ATG    2709
Cys Gly Ser Gly Ser Glu Val Tyr Tyr Pro Gly Thr Ala Asn Cys Met
                855                 860                 865

GAC GCT GAA GGA AAG CTG CGC CCA GAT CAG GAC TAT CTG ATG CAC ATC    2757
Asp Ala Glu Gly Lys Leu Arg Pro Asp Gln Asp Tyr Leu Met His Ile
            870                 875                 880

AGC CAC CGC TGG TCC CAT GAC GGC GCG AGG CAG ACC ATA GCG AAG CTC    2805
Ser His Arg Trp Ser His Asp Gly Ala Arg Gln Thr Ile Ala Lys Leu
885                 890                 895

ATG GGC GCT CAG GAC GGT TCA GGC GAC GCT GTC GAG CAG GAC GTG GCG    2853
Met Gly Ala Gln Asp Gly Ser Gly Asp Ala Val Glu Gln Asp Val Ala
900                 905                 910

TCC AGT AAT GCA CAC TGT GTC GCG TTC CTC ATC AAA GAC CCC CAA AAG    2901
Ser Ser Asn Ala His Cys Val Ala Phe Leu Ile Lys Asp Pro Gln Lys
915                 920                 925                 930

GTG AAA ACG GTC GAT GAG ATG AGG GAG CGG CTG AGG ATG CGT GGT CTC    2949
Val Lys Thr Val Asp Glu Met Arg Glu Arg Leu Arg Met Arg Gly Leu
                935                 940                 945

CGC TGC CAC ATC ATG TAC TGC AGG AAC TCG ACA AGG CTT CAG GTT GTC    2997
Arg Cys His Ile Met Tyr Cys Arg Asn Ser Thr Arg Leu Gln Val Val
            950                 955                 960

CCT CTG CTA GCA TCA AGG TCA CAG GCA CTC AGG TAT CTT TCC GTG CGC    3045
Pro Leu Leu Ala Ser Arg Ser Gln Ala Leu Arg Tyr Leu Ser Val Arg
965                 970                 975

TGG GGC GTA TCT GTG GGG AAC ATG TAT CTG ATC ACC GGG GAA CAT GGC    3093
Trp Gly Val Ser Val Gly Asn Met Tyr Leu Ile Thr Gly Glu His Gly
                980                 985                 990

GAC ACC GAT CTA GAG GAG ATG CTA TCC GGG CTA CAC AAG ACC GTG ATC    3141
Asp Thr Asp Leu Glu Glu Met Leu Ser Gly Leu His Lys Thr Val Ile
995                 1000                1005                1010

GTC CGT GGC GTC ACC GAG AAG GGT TCG GAA GCA CTG GTG AGG AGC CCA    3189
Val Arg Gly Val Thr Glu Lys Gly Ser Glu Ala Leu Val Arg Ser Pro
            1015                1020                1025

GGA AGC TAC AAG AGG GAC GAT GTC GTC CCG TCT GAG ACC CCC TTG GCT    3237
Gly Ser Tyr Lys Arg Asp Asp Val Val Pro Ser Glu Thr Pro Leu Ala
                1030                1035                1040

GCG TAC ACG ACT GGT GAG CTG AAG GCC GAC GAG ATC ATG CGG GCT CTG    3285
Ala Tyr Thr Thr Gly Glu Leu Lys Ala Asp Glu Ile Met Arg Ala Leu
            1045                1050                1055

AAG CAA GTC TCC AAG ACT TCC AGC GGC ATG TGAATTTGAT GCTTCTTTTA     3335
Lys Gln Val Ser Lys Thr Ser Ser Gly Met
        1060                1065

CATTTTGTCC TTTTCTTCAC TGCTATATAA AATAAGTTGT GAACAGTACC GCGGGTGTGT  3395

ATATATATAT TGCAGTGACA AATAAAACAG GACACTGCTA ACTATACTGG TGAATATACG  3455

ACTGTCAAGA TTGTATGCTA AGTACTCCAT TTCTCAATGT ATCAATCGGA ATTC       3509

(2) INFORMATION FOR SEQ ID NO:7:

(i) SEQUENCE CHARACTERISTICS:
        (A) LENGTH: 1068 amino acids
```

(B) TYPE: amino acid
(D) TOPOLOGY: linear (ii) MOLECULE TYPE: protein (xi) SEQUENCE DESCRIPTION: SEQ ID NO:7:

```
Met Ala Gly Asn Glu Trp Ile Asn Gly Tyr Leu Glu Ala Ile Leu Asp
  1               5                  10                  15

Ser His Thr Ser Ser Arg Gly Ala Gly Gly Gly Gly Gly Gly Gly Asp
             20                  25                  30

Pro Arg Ser Pro Thr Lys Ala Ala Ser Pro Arg Gly Ala His Met Asn
         35                  40                  45

Phe Asn Pro Ser His Tyr Phe Val Glu Glu Val Val Lys Gly Val Asp
     50                  55                  60

Glu Ser Asp Leu His Arg Thr Trp Ile Lys Val Val Ala Thr Arg Asn
 65                  70                  75                  80

Ala Arg Glu Arg Ser Thr Arg Leu Glu Asn Met Cys Trp Arg Ile Trp
                 85                  90                  95

His Leu Ala Arg Lys Lys Lys Gln Leu Glu Leu Glu Gly Ile Gln Arg
                100                 105                 110

Ile Ser Ala Arg Arg Lys Glu Gln Glu Gln Val Arg Arg Glu Ala Thr
            115                 120                 125

Glu Asp Leu Ala Glu Asp Leu Ser Glu Gly Glu Lys Gly Asp Thr Ile
130                 135                 140

Gly Glu Leu Ala Pro Val Glu Thr Thr Lys Lys Lys Phe Gln Arg Asn
145                 150                 155                 160

Phe Ser Asp Leu Thr Val Trp Ser Asp Asp Asn Lys Glu Lys Lys Leu
                165                 170                 175

Tyr Ile Val Leu Ile Ser Val His Gly Leu Val Arg Gly Glu Asn Met
                180                 185                 190

Glu Leu Gly Arg Asp Ser Asp Thr Gly Gly Gln Val Lys Tyr Val Val
            195                 200                 205

Glu Leu Ala Arg Ala Met Ser Met Met Pro Gly Val Tyr Arg Val Asp
210                 215                 220

Leu Phe Thr Arg Gln Val Ser Ser Pro Asp Val Asp Trp Ser Tyr Gly
225                 230                 235                 240

Glu Pro Thr Glu Met Leu Cys Ala Gly Ser Asn Asp Gly Glu Gly Met
                245                 250                 255

Gly Glu Ser Gly Gly Ala Tyr Ile Val Arg Ile Pro Cys Gly Pro Arg
            260                 265                 270

Asp Lys Tyr Leu Lys Lys Glu Ala Leu Trp Pro Tyr Leu Gln Glu Phe
        275                 280                 285

Val Asp Gly Ala Leu Ala His Ile Leu Asn Met Ser Lys Ala Leu Gly
    290                 295                 300

Glu Gln Val Gly Asn Gly Arg Pro Val Leu Pro Tyr Val Ile His Gly
305                 310                 315                 320

His Tyr Ala Asp Ala Gly Asp Val Ala Ala Leu Leu Ser Gly Ala Leu
                325                 330                 335

Asn Val Pro Met Val Leu Thr Gly His Ser Leu Gly Arg Asn Lys Leu
                340                 345                 350

Glu Gln Leu Leu Lys Gln Gly Arg Met Ser Lys Glu Ile Asp Ser
            355                 360                 365

Thr Tyr Lys Ile Met Arg Arg Ile Glu Gly Glu Leu Ala Leu Asp
        370                 375                 380

Ala Ser Glu Leu Val Ile Thr Ser Thr Arg Gln Glu Ile Asp Glu Gln
```

-continued

```
       385                 390                 395                 400
Trp Gly Leu Tyr Asp Gly Phe Asp Val Lys Leu Glu Lys Val Leu Arg
                    405                 410                 415
Ala Arg Ala Arg Arg Gly Val Ser Cys His Gly Arg Tyr Met Pro Arg
                420                 425                 430
Met Val Val Ile Pro Pro Gly Met Asp Phe Ser Asn Val Val His
            435                 440                 445
Glu Asp Ile Asp Gly Asp Val Lys Asp Ile Val Gly Leu
450                 455                 460
Glu Gly Ala Ser Pro Lys Ser Met Pro Pro Ile Trp Ala Glu Val Met
465                 470                 475                 480
Arg Phe Leu Thr Asn Pro His Lys Pro Met Ile Leu Ala Leu Ser Arg
                    485                 490                 495
Pro Asp Pro Lys Lys Asn Ile Thr Thr Leu Val Lys Ala Phe Gly Glu
                500                 505                 510
Cys Arg Pro Leu Arg Glu Leu Ala Asn Leu Thr Leu Ile Met Gly Asn
                515                 520                 525
Arg Asp Asp Ile Asp Asp Met Ser Ala Gly Asn Ala Ser Val Leu Thr
                530                 535                 540
Thr Val Leu Lys Leu Ile Asp Lys Tyr Asp Leu Tyr Gly Ser Val Ala
545                 550                 555                 560
Phe Pro Lys His His Asn Gln Ala Asp Val Pro Glu Ile Tyr Arg Leu
                    565                 570                 575
Ala Ala Lys Met Lys Gly Val Phe Ile Asn Pro Ala Leu Val Glu Pro
                580                 585                 590
Phe Gly Leu Thr Leu Ile Glu Ala Ala His Gly Leu Pro Ile Val
                595                 600                 605
Ala Thr Lys Asn Gly Gly Pro Val Asp Ile Thr Asn Ala Leu Asn Asn
                610                 615                 620
Gly Leu Leu Val Asp Pro His Asp Gln Asn Ala Ile Ala Asp Ala Leu
625                 630                 635                 640
Leu Lys Leu Val Ala Asp Lys Asn Leu Trp Gln Glu Cys Arg Arg Asn
                    645                 650                 655
Gly Leu Arg Asn Ile His Leu Tyr Ser Trp Pro Glu His Cys Arg Thr
                660                 665                 670
Tyr Leu Thr Arg Val Ala Gly Cys Arg Leu Arg Asn Pro Arg Trp Leu
            675                 680                 685
Lys Asp Thr Pro Ala Asp Ala Gly Ala Asp Glu Glu Phe Leu Glu
690                 695                 700
Asp Ser Met Asp Ala Gln Asp Leu Ser Leu Arg Leu Ser Ile Asp Gly
705                 710                 715                 720
Glu Lys Ser Ser Leu Asn Thr Asn Asp Pro Leu Trp Phe Asp Pro Gln
                    725                 730                 735
Asp Gln Val Gln Lys Ile Met Asn Asn Ile Lys Gln Ser Ser Ala Leu
                740                 745                 750
Pro Pro Ser Met Ser Ser Val Ala Ala Glu Gly Thr Gly Ser Thr Met
                755                 760                 765
Asn Lys Tyr Pro Leu Leu Arg Arg Arg Arg Leu Phe Val Ile Ala
770                 775                 780
Val Asp Cys Tyr Gln Asp Asp Gly Arg Ala Ser Lys Lys Met Leu Gln
785                 790                 795                 800
Val Ile Gln Glu Val Phe Arg Ala Val Arg Ser Asp Ser Gln Met Phe
                    805                 810                 815
```

```
Lys Ile Ser Gly Phe Thr Leu Ser Thr Ala Met Pro Leu Ser Glu Thr
            820                 825                 830

Leu Gln Leu Leu Gln Leu Gly Lys Ile Pro Ala Thr Asp Phe Asp Ala
        835                 840                 845

Leu Ile Cys Gly Ser Gly Ser Glu Val Tyr Tyr Pro Gly Thr Ala Asn
    850                 855                 860

Cys Met Asp Ala Glu Gly Lys Leu Arg Pro Asp Gln Asp Tyr Leu Met
865                 870                 875                 880

His Ile Ser His Arg Trp Ser His Asp Gly Ala Arg Gln Thr Ile Ala
            885                 890                 895

Lys Leu Met Gly Ala Gln Asp Gly Ser Gly Asp Ala Val Glu Gln Asp
        900                 905                 910

Val Ala Ser Ser Asn Ala His Cys Val Ala Phe Leu Ile Lys Asp Pro
    915                 920                 925

Gln Lys Val Lys Thr Val Asp Glu Met Arg Glu Arg Leu Arg Met Arg
930                 935                 940

Gly Leu Arg Cys His Ile Met Tyr Cys Arg Asn Ser Thr Arg Leu Gln
945                 950                 955                 960

Val Val Pro Leu Leu Ala Ser Arg Ser Gln Ala Leu Arg Tyr Leu Ser
                965                 970                 975

Val Arg Trp Gly Val Ser Val Gly Asn Met Tyr Leu Ile Thr Gly Glu
        980                 985                 990

His Gly Asp Thr Asp Leu Glu Glu Met Leu Ser Gly Leu His Lys Thr
            995                 1000                1005

Val Ile Val Arg Gly Val Thr Glu Lys Gly Ser Glu Ala Leu Val Arg
    1010                1015                1020

Ser Pro Gly Ser Tyr Lys Arg Asp Asp Val Val Pro Ser Glu Thr Pro
1025                1030                1035                1040

Leu Ala Ala Tyr Thr Thr Gly Glu Leu Lys Ala Asp Glu Ile Met Arg
                1045                1050                1055

Ala Leu Lys Gln Val Ser Lys Thr Ser Ser Gly Met
            1060                1065

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Possible peptide
            encoding
            sequences"

(iii) HYPOTHETICAL: YES (xi) SEQUENCE DESCRIPTION: SEQ ID NO:8:

WSNATGCCNC CNATHTGGGC NGARGTNATG MGN                              33

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Possible peptide
            encoding
```

-continued sequences"

(iii) HYPOTHETICAL: YES (xi) SEQUENCE DESCRIPTION: SEQ ID NO:9:

YTNMGNCCNG AYCARGAYTA YYTNATGCAY ATHWSNCAYM GN            42

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic
            oligonucleotide
            mixture"

(xi) SEQUENCE DESCRIPTION: SEQ ID NO:10:

ATGCCNCCNA THTGGGCNGA                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic
            oligonucleotide
            mixture"

(xi) SEQUENCE DESCRIPTION: SEQ ID NO:11:

TGCATNAGRT ARTCYTGRTC                                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic
            oligonucleotide
            mixture"

(xi) SEQUENCE DESCRIPTION: SEQ ID NO:12:

TCNGCCCADA TNGGNGGCAT                                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic
            oligonucleotide
            mixture"

(xi) SEQUENCE DESCRIPTION: SEQ ID NO:13:

GAYCARGAYT AYCTNATGCA                                    20

```
(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic
            oligonucleotide
            mixture"

(xi) SEQUENCE DESCRIPTION: SEQ ID NO:14:

TGRTCNGGNC KNAR                                                              14
```